United States Patent
Drizin et al.

(10) Patent No.: US 8,815,869 B2
(45) Date of Patent: *Aug. 26, 2014

(54) LACTAM ACETAMIDES AS CALCIUM CHANNEL BLOCKERS

(75) Inventors: Irene Drizin, Wadsworth, IL (US); George Doherty, Libertyville, IL (US); Pramila A. Bhatia, Libertyville, IL (US); Andrew O. Stewart, Libertyville, IL (US)

(73) Assignee: AbbVie Inc., North Chicago, IL (US)

( * ) Notice: Subject to any disclaimer, the term of this patent is extended or adjusted under 35 U.S.C. 154(b) by 286 days.

This patent is subject to a terminal disclaimer.

(21) Appl. No.: 13/045,010

(22) Filed: Mar. 10, 2011

(65) Prior Publication Data

US 2011/0230459 A1    Sep. 22, 2011

Related U.S. Application Data

(60) Provisional application No. 61/315,151, filed on Mar. 18, 2010.

(51) Int. Cl.
| | |
|---|---|
| *A61K 31/496* | (2006.01) |
| *A61K 31/454* | (2006.01) |
| *A61K 31/4545* | (2006.01) |
| *A61K 31/437* | (2006.01) |
| *C07D 401/06* | (2006.01) |
| *C07D 401/12* | (2006.01) |
| *C07D 471/04* | (2006.01) |
| *C07D 471/10* | (2006.01) |
| *C07D 487/04* | (2006.01) |
| *C07D 403/06* | (2006.01) |
| *C07D 471/08* | (2006.01) |
| *C07D 211/76* | (2006.01) |
| *A61K 31/4985* | (2006.01) |
| *A61K 31/4025* | (2006.01) |
| *C07D 403/12* | (2006.01) |

(52) U.S. Cl.
CPC ............ *C07D 211/76* (2013.01); *C07D 403/06* (2013.01); *C07D 471/08* (2013.01); *C07D 401/06* (2013.01); *C07D 487/04* (2013.01); *C07D 471/10* (2013.01); *C07D 401/12* (2013.01); *C07D 471/04* (2013.01)
USPC ...... 514/253.12; 514/278; 514/300; 514/322; 514/326; 514/316; 514/249; 514/422; 544/349; 544/360; 548/518; 546/16; 546/113; 546/188; 546/199; 546/208

(58) Field of Classification Search
None
See application file for complete search history.

(56) References Cited

U.S. PATENT DOCUMENTS 5,229,388 A    7/1993  Hrib et al.

| 8,044,069 | B2* | 10/2011 | Bhatia et al. ............... 514/317 |
|---|---|---|---|
| 2001/0029258 | A1 | 10/2001 | Snutch |
| 2005/0148587 | A1 | 7/2005 | Fraser et al. |
| 2010/0130558 | A1 | 5/2010 | Stewart |

FOREIGN PATENT DOCUMENTS

| WO | WO0059882 A1 | 10/2000 |
|---|---|---|
| WO | WO2007030061 A1 | 3/2007 |
| WO | 2007125398 A2 | 11/2007 |
| WO | 2008043533 A2 | 4/2008 |
| WO | 2008046527 A1 | 4/2008 |
| WO | WO-2009045382 A1 | 4/2009 |
| WO | WO-2010039947 A1 | 4/2010 |

OTHER PUBLICATIONS

Zamponi et al. Bioorganic & Medicinal Chemistry Letters, vol. 19, p. 6467-6472 (2009).*
Triggle, Biochemical Pharmacology vol. 74, p. 1-9 (2007).*
Angeli F., et al., "Calcium Channel Blockade to Prevent Stroke in Hypertension," American Journal of Hypertension, 2004, vol. 17 (9), pp. 817-822.
Arulmozhi D.K., et al., "Migraine: Current Concepts and Emerging Therapies," Vascular Pharmacology, 2005, vol. 43 (3), pp. 176-187.
Bao J., et al., "Differences in Ca2+ Channels Governing Generation of Miniature and Evoked Excitatory Synaptic Currents in Spinal Laminae I and II," The Journal of Neuro Science, 1998, vol. 18 (21), pp. 8740-8750.
Barone F.C., et al., "SB 201823-A Antagonizes Calcium Currents in Central Neurons and Reduces the Effects of Focal Ischemia in Rats and Mice," Stroke, 1995, vol. 26 (9), pp. 1683-1690.
Bell T.J., et al., "Cell Specific Alternative Splicing Increases Calcium Channel Current Density in the Pain Pathway," Neuron, 2004, vol. 41, pp. 127-138.
Berge, S. M. et al., "Pharmaceutical Salts," Journal of Pharmaceutical Sciences, 1977, vol. 66 (1), pp. 1-19.
Beuckmann C.T., et al., "N-Type Calcium Channel $\alpha_{1B}$ Subunit(Ca$_v$2.2) Knock-Out Mice Display Hyperactivity and Vigilance State Differences," The Journal of Neuro Science, 2003, vol. 23 (17), pp. 6793-6797.
Bhatia R., et al., "Fresh and Globular Amyloid β Protein (1-42) Induces Rapid Cellular Degeneration: Evidence for ABP Channel-Mediated Cellular Toxicity," The FASEB Journal, 2000, vol. 14 (9), pp. 1233-1243.

(Continued)

Primary Examiner — Emily Bernhardt

(57) ABSTRACT

The present application relates to calcium channel inhibitors containing compounds of formula (I)

(I)

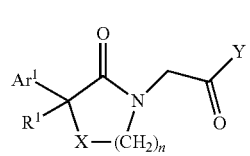

wherein $Ar^1$, n, $R^1$, X and Y are as defined in the specification. The present application also relates to compositions comprising such compounds, and methods of treating conditions and disorders using such compounds and compositions.

7 Claims, No Drawings

(56) References Cited

OTHER PUBLICATIONS

Bhattacharjee A., et al., "T-Type Calcium Channels Facilitate Insulin Secretion by Enhancing General Excitability in the Insulin-Secreting B-Cell Line, INS-1," Endocrinology, 1997, vol. 138 (9), pp. 3735-3740.
Bilici D., et al., "Protective Effect of T-Type Calcium Channel Blocker in Histamine-Induced Paw Inflammation in Rat," Pharmacological Research, 2001, vol. 44 (6), pp. 527-531.
Bowersox S.S., et al., "Selective N-Type Neuronal Voltage-Sensitive Calcium Channel Blocker SNX-111 Produces Spinal Antinociception in Rat Models of Acute Persistent and Neuropathic Pain," The Journal of Pharmacology and Experimental Therapeutics, 1996, vol. 279 (3), pp. 1243-1249.
Bunnelle W.H., et al., "Structure-Activity Studies and Analgesic Efficacy of N-(3-pyridinyl)-Bridged Bicyclic Diamines, Exceptionally Potent Agonists at Nicotinic Acetylcholine Receptors," Journal of Medicinal Chemistry, 2007, vol. 50, pp. 3627-3644.
Castiglioni A.J., et al., "Alternative Splicing in the C-Terminus of $Ca_v2.2$ Controls Expression and Gating of N-Type Calcium Channels," The Journal of Physiology, 2006, vol. 576 (1), pp. 119-134.
Cavalli A., et al., "Multi-Target Directed Ligands to Combat Neurodegenerative Diseases," Journal of Medicinal Chemistry, 2008, vol. 51 (3), pp. 347-372.
Chaplan S.R., et al., "Quantitative Assessment of Tactile Allodynia in the Rat Paw," Journal of Neuroscience Methods, 1994, vol. 53, pp. 55-63.
Chaplan S.R., et al., "Role of Voltage-Dependent Calcium Channel Subtypes in Experimental Tactile Allodynia," The Journal of Pharmacology and Experimental Therapeutics, 1994, vol. 269 (3), pp. 1117-1123.
Cizkova D., et al., "Localization of N-Type Ca2+ Channels in the Rat Spinal Cord Following Chronic Constrictive Nerve Injury," Experimental Brain Research, 2002, vol. 147 (4), pp. 456-463.
Colbourne F., et al., "Continuing Postischemic Neuronal Death in CA1: Influence of Ischemia Duration and Cytoprotective Doses of NBQX and SNX-111 in Rats," Stroke, 1999, vol. 30 (3), pp. 662-668.
Croom K.F., et al., "A Review of the Use of Modified-Release Formulations in the Treatment of Hypertension and Angina Pectoris," Drugs, 2006, vol. 66 (4), pp. 497-528.
Cross, L.C. et al., "IUPAC Commission on Nomenclature of Organic Chemistry: Rules for the Nomenclature of Organic Chemistry, Section E: Stereochemistry," Pure and Applied Chemistry, 1976, vol. 45, pp. 13-30.
Darszon A., et al., "Ion Channels in Sperm Physiology," Physiological Reviews, 1999, vol. 79 (2), pp. 481-510.
Dolphin A.C., "A Short History of Voltage-Gated Calcium Channels," British Journal of Pharmacology, 2006, vol. 147, pp. S56-S62.
Eliel, E. L. et al., "Stereochemistry of Organic Compounds," 1994, John Wiley & Sons, Inc. New York. Table of Contents.
Evans A.R., et al., "Differential Regulation of Evoked Peptide Release by Voltage-Sensitive Calcium Channels in Rat Sensory Neurons," Brain Research, 1996, vol. 712 (2), pp. 265-273.
Feng Z.P., et al., "Determinants of Inhibition of Transiently Expressed Voltage-Gated Calcium Channels by ω-Conotoxins GVIA and MVIIA," The Journal of Biological Chemistry, 2003, vol. 278 (22), pp. 20171-20178.
Geldenhuys W.J., et al., "Structure-Activity Relationships of Pentacycloundecylamines at the N-Methyl-D-Aspartate Receptor," Bioorganic and Medicinal Chemistry, 2007, vol. 15 (3), pp. 1525-1532.
Gitlin M., "Treatment-Resistant Bipolar Disorder," Molecular Psychiatry, 2006, vol. 11 (3), pp. 227-240.
Gladstone J.P., et al., "Current and Emerging Treatment Options for Migraine and Other Primary Headache Disorders," Expert Revies of Neurotherapeutics, 2003, vol. 3 (6), pp. 845-872.
Gould R.J., et al., "Antischizophrenic Drugs of the Diphenylbutylpiperidine Type Act As Calcium Channel Antagonists," Proceeding of the National Academy of Sciences of the USA, 1983, vol. 80 (16), pp. 5122-5125.
Gray A.C., et al., "Neuronal Calcium Channels: Splicing for Optimal Performance," Cell Calcium, 2007, vol. 42 (4-5), pp. 409-417.
Greene, T.W., et al., Protective Groups in Organic Synthesis, 3rd Edition, John Wiley and Sons, Inc., 1999, Table of Contents.
Hatakeyama S., et al., "Differential Nociceptive Responses in Mice Lacking the α 1B Subunit of N-Type Ca2+ Channels," Neuroreport, 2001, vol. 12 (11), pp. 2423-2427.
Heinemann U., et al., "Extracellular Free Calcium and Potassium during Paroxysmal Activity in the Cerebral Cortex of the Cat," Experimental Brain Research, 1977, vol. 27 (3-4), pp. 237-243.
Heinke B., et al., "Pre-and Postsynaptic Contributions of Voltage-Dependent Ca2+ Channels to Nociceptive Transmission in Rat Spinal Laminal Neurons," The European Journal of Neurosciences, 2004, vol. 19 (1), pp. 103-111.
Ino M., et al., "Functional Disorders of the Sympathetic Nervous System in Mice Lacking the A1B Subunit ($Ca_v2.2$) of N-Type Calcium Channels," Proceeding of the National Academy of Sciences of the USA, 2001, vol. 98 (9), pp. 5323-5328.
Kim C., et al., "Altered Nociceptive Response in Mice Deficient in the $α_{1B}$ Subunit of the Voltage-Dependent Calcium Channel," Molecular and Cellular Neurosciences, 2001, vol. 18 (2), pp. 235-245.
Levy N.A., et al., "Calcium Channel Antagonists for the Treatment of Bipolar Disorder," Bipolar Disorders, 2000, vol. 2 (2), pp. 108-119.
Little H.J., et al., "Calcium Channel Antagonists Decrease the Ethanol Withdrawal Syndrome," Life Sciences, 1986, vol. 39 (22), pp. 2059-2065.
Liu L., et al., "In Vivo Analysis of Voltage-Dependent Calcium Channels," Journal of Bioenegetics and Biomembrances, 2003, vol. 35 (6), pp. 671-685.
Lorton D., "β-Amyloid-Induced II-1 β Release from an Activated Human Monocyte Cell Line is Calcium-and G-Protein-Dependent," Mechanisms of Ageing and Development, 1997, vol. 94 (1-3), pp. 199-211.
Lubin M.L., et al., "A Nonadherent Cell-Based HTS Assay for N-Type Calcium Channel using Calcium 3 Dye," Assay and Drug Development Technologies, 2006, vol. 4 (6), pp. 689-694.
Luebke J.I., et al., "Multiple Calcium Channel Types Control Glutamatergic Synaptic Transmission in the Hippocampus," Neuron, 1993, vol. 11 (5), pp. 895-902.
Luo Z.D., et al., "Upregulation of Dorsal Root Ganglion A2D Calcium Channel Subunit and its Correlation with Allodynia in Spinal Nerve-Injured Rats," The Journal of Neuro Science, 2001, vol. 21 (6), pp. 1868-1875.
Malmberg A.B., et al., "Voltage-Sensitive Calcium Channels in Spinal Nociceptive Processing: Blockade of N-and P-Type Channels Inhibits Formalin-Induced Nociception," The Journal of Neuro Science, 1994, vol. 14 (8), pp. 4882-4890.
Mason R.P., et al., "Antioxidant and Cytoprotective Activities of the Calcium Channel Blocker Mibefradil," Biochemical Pharmacology, 1998, vol. 55 (11), pp. 1843-1852.
Matthews E.A., et al., "Effects of Spinally Delivered N- and P-Type Voltage-Dependent Calcium Channel Antagonists on Dorsal Horn Neuronal Responses in a Rat Model of Neuropathy," Pain, 2001, vol. 92 (1-2), pp. 235-246.
McGivern J.G., "Targeting N-Type and T-Type Calcium Channels for the Treatment of Pain," Drug Discovery Today, 2006, vol. 11 (5-6), pp. 245-253.
Miljanich G.P.,et al., "Antagonists of Neuronal Calcium Channels: Structure Function and Therapeutic Implications," Annual Review of Pharmacology and Toxicology, 1995, vol. 35, pp. 707-734.
Newton R.A., et al., "Dorsal Root Ganglion Neurons Show Increased Expression of the Calcium Channel A2D-1 Subunit Following Partial Sciatic Nerve Injury," Molecular Brain Research, 2001, vol. 95 (1-2), pp. 1-8.
Ohnmacht C.J., et al., "Synthesis and Carbon-13 NMR Study of 2-Benzyl, 2-Methyl, 2-Aryloctahydropyrrolo[3,4-c]pyrroles and the 1,2,3,5-Tetrahydropyrrolo[3,4-c]pyrrole Ring System," Journal of Heterocyclic Chemistry, 1983, vol. 20, pp. 321-329.
Olivera B.M., et al., "Calcium Channel Diversity and Neurotransmitter Release: The ω-Conotoxins ω-Agatoxins," Annual Review of Biochemistry, 1994, vol. 63, pp. 823-867.

(56) References Cited

OTHER PUBLICATIONS

Otoom S., et al., "Nifedipine Inhibits Picrotoxin-Induced Seizure Activity: Further Evidence on the Involvement of L-Type Calcium Channel Blockers in Epilepsy," Fundamental & Clinical Pharmacology, 2006, vol. 20 (2), pp. 115-119.
Pietrobon D., "Function and Dysfunction of Synaptic Calcium Channels: Insights from Mouse Models," Current Opinion in Neurobiology, 2005, vol. 15 (3), pp. 257-265.
Prescott D.M., "Methods in Cell Biology", Academic Press, 1976, Table of Contents.
Raingo J., et al., "Alternative Splicing Controls G Protein-Dependent Inhibition of N-Type Calcium Channels in Nociceptors," Nature Neuroscience, 2007, vol. 10 (3), pp. 285-292.
Rodnitzky R.L., "Can Calcium Antagonists Provide a Neuroprotective Effect in Parkinson'S Disease?," Drugs, 1999, vol. 57 (6), pp. 845-849.
Saade S., et al., "The L-Type Calcium Channel Blocker Nimodipine Mitigates "Learned Helplessness" in Rats," Pharmacology, Biochemistry and Behavior, 2003, vol. 74 (2), pp. 269-278.
Saegusa H., et al., "Suppression of Inflammatory and Neuropathic Pain Symptoms in Mice Lacking the N-Type $CA^{2+}$ Calcium Channel," The EMBO Journal, 2001, vol. 20 (10), pp. 2349-2356.
Scott D.A., et al., "Actions of Intrathecal ω-Conotoxins CVID GVIA MVIIA and Morphine in Acute and Neuropathic Pain in the Rat," European Journal of Pharmacology, 2002, vol. 451 (3), pp. 279-286.
Shin H.S., et al., "T-type $Ca^{2+}$ Channels as Therapeutic Targets in the Nervous System," Current Opinion in Pharmacology, 2008, vol. 8 (1), pp. 33-41.
Smith M.T., et al., "The Novel N-Type Calcium Channel Blocker, AM336, Produces Potent Dose-Dependent Antinociception after Intrathecal Dosing in Rats and Inhibits Substance P Release in Rat Spinal Cord Slices," Pain, 2002, vol. 96 (1-2), pp. 119-127.
Stamm H., et al., "Einstufensynthese Von Pyrrolidonen Durch Amidoethylierung Einfacher Ester mit N-Acylaziridinen," Chemische Berichte, 1981, vol. 114, pp. 32-48.
Takahashi T., et al., "Different Types of Calcium Channels Mediate Central Synaptic Transmission," Nature, 1993, vol. 366 (6451), pp. 156-158.
Takei T., et al., "Increased Sensitivity to Halothane but Decreased Sensitivity to Propofol in Mice Lacking the N-Type $Ca^{2+}$ Channel," Neuroscience Letters, 2003, vol. 350 (1), pp. 41-45.
Tort A.B., et al., "Atypical Antipsychotic Profile of Flunarizine in Animal Models," Psychopharmacology, 2005, vol. 177 (3), pp. 344-348.
Urban M.O., et al., "Medullary N-Type and P/Q-Type Calcium Channels Contribute to Neuropathy-Induced Allodynia," Neuroreport, 2005, vol. 16 (6), pp. 563-566.
Vagnucci A.H., et al., "Alzheimer's Disease and Angiogenesis," The Lancet, 2003, vol. 361 (9357), pp. 605-608.
Veng L.M., et al., "Age-Related Working Memory Impairment is Correlated with Increases in the L-Type Calcium Channel Protein A1D ($Ca_v1.3$) in Area Ca1 of the Hippocampus and both are Ameliorated by Chronic Nimodipine Treatment," Molecular Brain Research, 2003, vol. 110 (2), pp. 193-202.
Vezzani A., . et al., "Effects of Various Calcium Channel Blockers on Three Different Models of Limbic Seizures in Rats," Neuropharmacology, 1988, vol. 27 (5), pp. 451-458.
Wang Y.X., et al., "Effects of Intrathecal Administration of Ziconotide a Selective Neuronal N-Type Calcium Channel Blocker on Mechanical Allodynia and Heat Hyperalgesia in a Rat Model of Postoperative Pain," Pain, 2000, vol. 84 (2-3), pp. 151-158.
Westenbroek R.E., et al., "Localization of $Ca^{2+}$ Channel Subtypes on Rat Spinal Motor Neurons Interneurons and Nerve Terminals," The Journal of Neuro Science, 1998, vol. 18 (16), pp. 6319-6330.
Yamamoto T., et al., "Differential Effects of Intrathecally Administered N- and P-Type Voltage-Sensitive Calcium Channel Blockers upon Two Models of Experimental Mononeuropathy in the Rat," Brain Research, 1998, vol. 794 (2), pp. 329-332.
Yokoyama K., et al., "Plastic Change of N-Type Ca Calcium Channel Expression after Preconditioning is Responsible for Prostaglandin $E_2$-Induced Long-Lasting Allodynia," Anesthesiology, 2003, vol. 99 (6), pp. 1364-1370.
Zanchetti A., et al., "Calcium Antagonist Lacidipine Slows Down Progression of Asymptomatic Carotid Atherosclerosis. Principal Results of the European Lacidipine Study on Atherosclerosis (ELSA), A Randomized, Double-Blind, Long-Term Trial," Circulation, 2002, vol. 106 (19), pp. 2422-2427.
Cox. B. et al.; Expert Opinion on Therapeutic Patents 1998, vol. 8, No. 10, pp. 1237-1250.
International Search Report for PCT/US2011/027905 dated Apr. 18, 2011.
Written Opinion for PCT/US2011/027905 dated Sep. 18. 2012.
Barberis et al., "Synthesis of a novel series of 4,4-disubstituted 2,3,4,7-tetrahydroazepines," Tetrahedron Letters 2005, 46(29): 4847-4850.
De Filippis et al., "Palladium-catalyzed [alpha]-arylation of N-protected 2-piperidinones," Tetrahedron 2004, 60(43): 9757-9767.
Walsh et al., "Synthesis and antiallergy activity of 4-(diarylhydroxymethyl)-1-[3-(aryloxy)propyl]piperidines and structurally related compounds," J. Med. Chem. 1989, 32(1): 105-118.

* cited by examiner

LACTAM ACETAMIDES AS CALCIUM CHANNEL BLOCKERS

CROSS REFERENCE SECTION TO RELATED APPLICATIONS

This application claims priority to U.S. Provisional Patent Application Ser. No. 61/315,151 filed Mar. 18, 2010, which is incorporated herein by reference in its entirety.

TECHNICAL FIELD

The present application relates to compounds that are calcium channel blockers, compositions comprising such compounds, and methods of treating conditions and disorders using such compounds and compositions.

BACKGROUND OF THE INVENTION

Voltage-gated calcium channels (VGCC) play an integral role in the regulation of membrane ion conductance, neurotransmitter release, and cellular excitability. VGCC are composed of the pore-forming α1 subunit and auxiliary α2δ and β subunits that modulate channel expression and functional properties (Dolphin, A C British Journal of Pharmacology 2006; 147 (Suppl. 1): S56-S62). These channels can be classified into low-voltage activated (LVA; T-type or $Ca_v3.x$) and high-voltage activated (HVA; L-type or $Ca_v1.x$ and N-, P/Q- and R-types or $Ca_v2.x$) channels. N-, P/Q and R channels typically activate at more positive membrane potentials (~−30 mV) and are involved in "presynaptic" neurotransmission (McGivern J G Drug Discovery Today 2006; 11: 245-253). T-type channels are activated at relatively negative membrane potentials (~−60 mV) and are primarily involved in "postsynaptic" excitability (Shin, H.-S.; et al. Curr. Opin. in Pharmacology 2008; 8: 33-41).

N-type channel $α_δ$ subunits are encoded by a single gene ($α_1B$ or $Ca_v2.2$) in contrast to pharmacologically defined L- and T-type currents that are encoded by multiple $α_1$-subunit genes. A diversity of N-type channels arises due to extensive alternative splicing of the α subunit gene that generates variants with different expression patterns and GPCR-modulated biophysical properties (Gray, A C; et al. Cell Calcium 2007; 42: 409-417). The primary sequence for $Ca_v2.2$ is highly conserved across species (rat and human share 91% identity at the amino acid level).

N-type channels are widely expressed in the central nervous system (CNS) (cortex, hippocampus, striatum, thalamus, brain stem nuclei and spinal cord) and in the peripheral nervous system (PNS) (adult sympathetic nervous system and dorsal root ganglia) (Ino, M; et al. Proc. Natl. Acad. Sci. USA 2001; 98: 5323-5328). In pain pathways, N-type channels are expressed in the rostral ventral medulla, an important site of descending pain modulation (Urban, M O; et al. Neuroreport 2005; 16: 563-566) and are a major contributor to the synaptic neurotransmission that occurs between C/Aδ nociceptors and spinal lamina I neurons (Bao, J; et al. J Neurosci. 1998; 18: 8740-50. Heinke, B; et al. Eur. J. Neurosci. 2004; 9: 03-111). In contrast, P/Q type channels are expressed almost exclusively in laminae II-IV of the spinal cord and show little co-localization with Substance P and N-type channels (Westenbroek, R E; et al. J. Neurosci. 1998; 18: 6319-6330).

Following nerve injury there is increased expression of $Ca_v2.2$ (Westenbroek, R E; et al. J. Neurosci. 1998; 18: 6319-6330. Cizkova, D; et al. Exp. Brain Res. 2002; 147: 456-463. Yokoyama, K; et al. Anesthesiology 2003; 99: 1364-1370.) and α2δ1 subunits (Luo, Z D; et al. J. Neurosci. 2001; 21: 1868-1875. Newton, R A; et al. Mol. Brain Res. 2001; 95: 1-8.) in addition to increases in the superficial layers of the dorsal horn of the spinal cord supporting a role for N-type channels in neuropathic pain. Recently a nociceptor-specific $Ca_v2.2$ splice variant has been identified in the dorsal root ganglion (Bell, T J; et al. Neuron 2004; 41: 127-138). These channels have distinct electrophysiological properties and current densities (Castiglioni, A J; et al. J. Physiol. 2006; 576(Pt 1): 119-134) compared to wildtype $Ca_v2.2$ channels. While G-protein coupled receptor inhibition of wildtype N-type channels is typically mediated by Gβγ and is voltage-dependent, the nociceptor specific splice variant is inhibited by GPCR activation (e.g. opioids) in a voltage-independent fashion (Raingo, J.; Castiglioni, A J; et al. Nat. Neurosci. 2007; 10: 285-292.). This mechanism substantially increases the sensitivity of $Ca_v2.2$ channels to opiates and gamma-aminobutyric acid (GABA) suggesting that cell-specific alternative splicing of mRNA for $Ca_v2.2$ channels serves as a molecular switch that controls the sensitivity of N-type channels to neurotransmitters and drugs that modulate nociception. Collectively these data provide further support for the role of $Ca_v2.2$ channels in pain states.

The relative contributions of various HVA $Ca^{2+}$ channels in nociceptive signaling have been evaluated using knockout mice studies. $Ca_v2.2$ knockout mice are healthy, fertile, and do not display overt neurological deficits (Ino, M; et al. Proc. Natl. Acad. Sci. USA 2001; 98: 5323-5328. Kim, C; et al. Mol. Cell. Neurosci. 2001; 18: 235-245. Hatakeyama, S; et al. Neuroreport 2001; 12: 2423-2427. Liu; L; et al. 2003; 35: 671-685.). This finding suggests that other types of $Ca_v$ channels are able to compensate for the lack of $Ca_v2.2$ channels at most synapses in these mice (Pietrobon, D Curr. Opin. Neurobiol. 2005; 15: 257-265). $Ca_v2.2$ deficient mice are resistant to the development of inflammatory and neuropathic pain (Kim, C; et al. Mol. Cell. Neurosci. 2001; 18: 235-245. Hatakeyama, S; et al. Neuroreport 2001; 12: 2423-2427. Saegusa, H; et al. EMBO J. 2001; 20: 2349-2356.), have decreased sympathetic nervous system function (Ino, M; et al. Proc. Natl. Acad. Sci. USA 2001; 98: 5323-5328), and altered responses to both ethanol and anesthetics (Newton, R A; et al. Brain Res. Mol. Brain Res. 2001; 95: 1-8. Takei, R; et al. Neurosci. Lett. 2003; 350: 41-45). Additional behavioral studies indicate that $Ca_v2.2$ knockout mice are less anxious, are hyperactive, and show enhanced vigilance compared to wild-type littermates (Beuckmann, C T; et al. J. Neurosci. 2003; 23: 6793-6797).

N- and P/Q-type channels are localized at neuronal synaptic junctions and contribute significantly to neurotransmitter release (Olivera, B M; et al. Annu Rev. Biochem. 1994; 63: 823-867. Miljanich, G P; et al. Annu Rev. Pharmacol. Toxicol. 1995; 35: 707-734). N-type channels play a major role in the release of glutamate, acetylcholine, dopamine, norepinephrine, GABA and calcitonin gene-related protein (CGRP). P/Q-type channels may be involved in the release of glutamate, aspartate, 5HT, GABA and probably glycine (Pietrobon, D Curr. Opin. Neurobiol. 2005; 15: 257-265).

L, P/Q and N-type channels are blocked by channel specific antagonists i.e., dihydropyridines, ω-agatoxin IVA and ω-conotoxin MVIIA/ziconotide, respectively. Agatoxin IVa has been shown to block excitatory (Luebke, J I; et al. Neuron 1993; 11: 895-902) as well as inhibitory neurotransmission (Takahashi, T; et al. Nature 1993; 366: 156-158). Intrathecal injection of selective N-type channel blockers (e.g. cono-toxin-derived peptides such as GVIA, MVIIA (ziconotide), and CVID) significantly attenuates pain responses in animal models of neuropathic pain, formalin-induced pain, and postoperative pain (Chaplan, S R; et al. J. Pharmacol. Exp. Ther.

1994; 269: 1117-1123. Malmberg, A B; et al. J. Neurosci. 1994; 14: 4882-4890. Bowersox, SS; et al. J. Pharmacol. Exp. Ther. 1996; 279: 1243-1249. Wang, Y X; et al. Pain 2000; 84: 151-158. Scott, D A; et al. Eur. J. Pharmacol. 2002; 451: 279-286.). These peptide blockers bind to the pore region of the channel, do not show voltage- or frequency-dependent activity, and show irreversible channel block (Feng, Z P; et al. J. Biol. Chem. 2003; 278: 20171-20178). Ziconotide potently blocks neurotransmitter release in the spinal cord dorsal horn (Matthews, E A; et al. Pain 2001; 92: 235-246. Smith, M T; et al. Pain 2002; 96: 119-127. Heinke, B; et al. Eur. J. Neurosci. 2004; 19: 103-111.) and in dorsal root ganglion (DRG) neurons (Evans, A R; et al. Brain Res. 1996; 712: 265-273. Smith, M T; et al. Pain 2002; 96: 119-127.). It also potently and fully blocks depolarization-induced release of substance P from rat spinal cord slices. In contrast, intrathecal delivery of the selective P/Q type blocker ω-agatoxin IVA had no effects on mechanical allodynia in the spinal nerve ligation model (Chaplan, S R; et al. J. Pharmacol. Exp. Ther. 1994; 269: 1117-1123) or thermal hyperalgesia in the chronic constriction injury model (Yamamoto, T; et al. Brain Res. 1998; 794: 329-332) of neuropathic pain.

Pain is the most common symptom of disease and the most frequent complaint with which patients present to physicians. Inadequate pain management across the spectrum of pain etiologies remains a major public health problem. Going forward, the development of novel therapeutics with new mechanisms of action for the treatment of pain including calcium channel blockade will have a significant impact on the ongoing struggle to balance efficacy and safety for those patients most in need.

SUMMARY OF THE INVENTION

The invention is directed to compounds of formula (I)

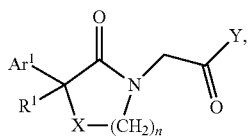

(I)

or a pharmaceutically acceptable salt thereof, wherein
n is 1 or 2;
X is $CH_2$, NC(O)OtBu, NH, N-alkyl, O, or $S(O)_r$;
r is 0, 1, or 2;
$R^1$ is hydrogen, alkyl, or $G^1$;
$Ar^1$ is aryl or heteroaryl; wherein $Ar^1$ is unsubstituted or further substituted with 1, 2, 3, 4, or 5 substituents independently selected from the group consisting of alkyl, alkenyl, alkynyl, halogen, —CN, —$NO_2$, —$OR^a$, —$S(R^c)$, —$S(O)(R^c)$, —$S(O)_2R^c$, —$S(O)_2N(R^b)_2$, —$C(O)R^b$, —$C(O)O(R^b)$, —$C(O)N(R^b)_2$, —$N(R^b)_2$, —$N(R^b)C(O)R^b$, —$N(R^b)C(O)O(R^b)$, —$N(R^b)S(O)_2R^c$, haloalkyl, —$(CR^dR^e)_m$—$OR^a$, —$(CR^dR^e)_m$—$S(R^c)$, —$(CR^dR^e)_m$—$S(O)(R^c)$, —$(CR^dR^e)_m$—$S(O)_2R^c$, —$(CR^dR^e)_m$—$S(O)_2N(R^b)_2$, —$(CR^dR^e)_m$—$C(O)R^b$, —$(CR^dR^e)_m$—$C(O)O(R^b)$, —$(CR^dR^e)_m$—$C(O)N(R^b)_2$, —$(CR^dR^e)_m$—$N(R^b)_2$, —$(CR^dR^e)_m$—$N(R^b)C(O)R^b$, —$(CR^dR^e)_m$—$N(R^b)C(O)O(R^b)$, and —$(CR^dR^e)_m$—$N(R^b)S(O)_2R^c$;

$R^a$, at each occurrence, is independently hydrogen, alkyl, haloalkyl, or —$(CR^dR^e)_m$—O(alkyl);
$R^b$, at each occurrence, is independently hydrogen, alkyl, haloalkyl, or $G^1$;
$R^c$, at each occurrence, is independently alkyl or haloalkyl;
$R^d$ and $R^e$, at each occurrence, are each independently hydrogen, halogen, alkyl, or haloalkyl;
m, at each occurrence, is independently 1, 2, 3, 4, 5, or 6;

Y is (i), (ii), (iii), (iv), (v), (vi), (vii), (viii), (ix), (x) or (xi);

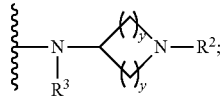

(i)

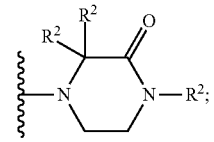

(ii)

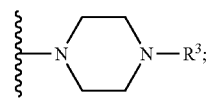

(iii)

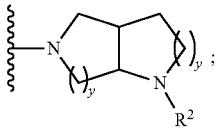

(iv)

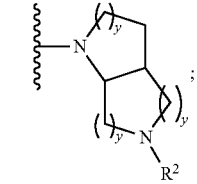

(v)

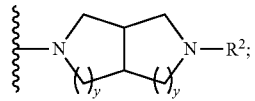

(vi)

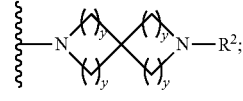

(vii)

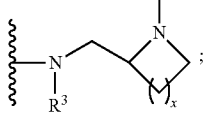

(viii)

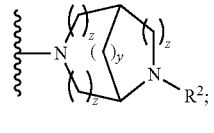

(ix)

(x)

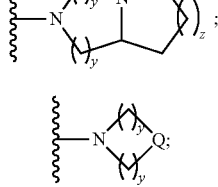

(xi)

x is 1, 2, or 3;
y at each occurrence, is independently 1 or 2;
z at each occurrence, is independently 0, 1, or 2;
Q is O, S, Or $CH_2$;
$R^2$, at each occurrence, is independently hydrogen or alkyl;
$R^3$ is hydrogen, alkyl, or $G^1$; and
$G^1$, at each occurrence, is independently aryl, heteroaryl, heterocycle, cycloalkyl, or cycloalkenyl; wherein each $G^1$ is independently unsubstituted or further substituted with 1, 2, 3, 4, 5, or 6 substituents independently selected from the group consisting of alkyl, alkenyl, alkynyl, halogen, oxo, —CN, —NO$_2$, —OR$^a$, —S(R$^c$), —S(O)(R$^c$), —S(O)$_2$R$^c$, —S(O)$_2$N(R$^b$)$_2$, C(O)R$^b$, —C(O)O(R$^b$), —C(O)N(R$^b$)$_2$, —N(R$^b$)$_2$, —N(R$^b$)C(O)R$^b$, —N(R$^b$)C(O)O(R$^b$), —N(R$^b$)S(O)$_2$R$^c$, haloalkyl, —(CR$^d$R$^e$)$_m$—OR$^a$, —(CR$^d$R$^e$)$_m$—S(R$^c$), —(CR$^d$R$^e$)$_m$—S(O)(R$^c$), —(CR$^d$R$^e$)$_m$—S(O)$_2$R$^c$, —(CR$^d$R$^e$)$_m$—S(O)$_2$N(R$^b$)$_2$, —(CR$^d$R$^e$)$_m$—C(O)R$^b$, —(CR$^d$R$^e$)$_m$—C(O)O(R$^b$), —(CR$^d$R$^e$)$_m$—C(O)N(R$^b$)$_2$, —(CR$^d$R$^e$)$_m$—N(R$^b$)$_2$, —(CR$^d$R$^e$)$_m$—N(R$^b$)C(O)R$^b$, —(CR$^d$R$^e$)$_m$—N(R$^b$)C(O)O(R$^b$), and —(CR$^d$R$^e$)$_m$—N(R$^b$)S(O)$_2$R$^c$.

Another aspect of the invention relates to pharmaceutical compositions comprising therapeutically effective amount of compound(s) of the invention or pharmaceutically acceptable salts thereof, in combination with one or more pharmaceutically acceptable carrier. Such compositions can be administered in accordance with a method of the invention, typically as part of a therapeutic regimen for treatment or prevention of conditions and disorders related to calcium channels. More particularly, the method is useful for treating conditions related to a method of treating pain in a subject in need thereof. The method comprises administering to the subject a therapeutically suitable amount of a compound of formula (I), or a pharmaceutically acceptable salt thereof. Conditions related to pain include acute pain, chronic pain, neuropathic pain, inflammatory pain, visceral pain, cancer pain, allodynia, fibromyalgia, sciatica, back pain, and headache pain including migraine, or combinations thereof.

Another aspect of the invention provides a method of treating disorders of the central nervous system in a subject in need thereof. The method comprising the step of: administering a therapeutically suitable amount of a compound of formula (I), or a pharmaceutically acceptable salt thereof. The disorders of the central nervous system include stroke, epilepsy, manic depression, bipolar disorders, depression, anxiety, schizophrenia, migraine, and psychoses; neural degenerative disorders including Alzheimer's disease, AIDS related dementia, Parkinson's disease, neuropathy caused by head injury, and dementia caused by cerebrovascular disorders; disorders of the lower urinary tract including overactive bladder, prostatis, prostadynia, interstitial cystitis, and benign prostatic hyperplasia; disorders caused by psychogenic stress including bronchial asthma, unstable angina, and hypersensitive colon inflammation; cardiovascular disorders including hypertension, atherosclerosis, heart failure, and cardiac arrhythmias; drug addiction withdrawal symptoms, including ethanol addiction withdrawal symptoms; skin disorders including pruritis and allergic dermatitis, inflammatory bowel disease; cancer; diabetes; and infertility and sexual dysfunction, or combinations thereof.

The compounds of the present invention are novel calcium channel blockers that have utility in treating pain, amongst other conditions. The compounds, compositions comprising the compounds, and methods for treating or preventing conditions and disorders by administering the compounds are further described herein.

DETAILED DESCRIPTION OF THE INVENTION

Compounds of formula (I) are disclosed in this invention

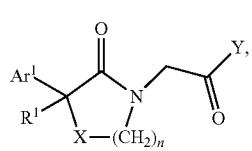

(I)

wherein Ar$^1$, n, R$^1$, X and Y are as defined above in the Summary of the Invention. Compositions comprising such compounds and methods for treating conditions and disorders using such compounds and compositions are also disclosed.

In various embodiments, the present invention provides at least one variable that occurs more than one time in any substituent or in the compound of the invention or any other formulae herein. Definition of a variable on each occurrence is independent of its definition at another occurrence. Further, combinations of substituents are permissible only if such combinations result in stable compounds. Stable compounds are compounds, which can be isolated from a reaction mixture.

a. Definitions

As used in the specification and the appended claims, unless specified to the contrary, the following terms have the meaning indicated:

The term "alkenyl" as used herein, means a straight or branched hydrocarbon chain containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkenylene" denotes a divalent group derived from a straight or branched chain hydrocarbon of 2 to 4 carbon atoms and contains at least one carbon-carbon double. Representative examples of alkenylene include, but are not limited to, —CH=CH— and —CH$_2$CH=CH—.

The term "alkyl" as used herein, means a straight or branched, saturated hydrocarbon chain containing from 1 to 10 carbon atoms. The term "lower alkyl" or "C$_{1-6}$ alkyl" means a straight or branched chain hydrocarbon containing 1 to 6 carbon atoms. The term "C$_{1-3}$ alkyl" means a straight or branched chain hydrocarbon containing 1 to 3 carbon atoms. Representative examples of alkyl include, but are not limited to, methyl, ethyl, n-propyl, isopropyl, n-butyl, sec-butyl, isobutyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylene" denotes a divalent group derived from a straight or branched chain hydrocarbon 1 to 10 carbon atoms. Representative examples of alkylene include, but are not limited to, —CH$_2$—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl" as used herein, means phenyl or a bicyclic aryl. The bicyclic aryl is naphthyl, or a phenyl fused to a monocyclic cycloalkyl, or a phenyl fused to a monocyclic cycloalkenyl. Representative examples of the aryl groups include, but are not limited to, dihydroindenyl, indenyl, naphthyl, dihydronaphthalenyl, and tetrahydronaphthalenyl. The bicyclic aryl is attached to the parent molecular moiety through any carbon atom contained within the bicyclic ring system. The aryl groups of the present invention can be unsubstituted or substituted.

The term "cycloalkyl" or "cycloalkane" as used herein, means a monocyclic, a bicyclic, or a tricyclic cycloalkyl. The monocyclic cycloalkyl is a carbocyclic ring system containing three to eight carbon atoms, zero heteroatoms and zero double bonds. Examples of monocyclic ring systems include cyclopropyl, cyclobutyl, cyclopentyl, cyclohexyl, cycloheptyl, and cyclooctyl. The bicyclic cycloalkyl is a monocyclic cycloalkyl fused to a monocyclic cycloalkyl ring, or a bridged monocyclic ring system in which two non-adjacent carbon atoms of the monocyclic ring are linked by an alkylene bridge containing one, two, three, or four carbon atoms. Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Tricyclic cycloalkyls are exemplified by a bicyclic cycloalkyl fused to a monocyclic cycloalkyl, or a bicyclic cycloalkyl in which two non-adjacent carbon atoms of the ring systems are linked by an alkylene bridge of 1, 2, 3, or 4 carbon atoms. Representative examples of tricyclic-ring systems include, but are not limited to, tricyclo[3.3.1.0$^{3,7}$]nonane(octahydro-2,5-methanopentalene or noradamantane), and tricyclo[3.3.1.1$^{3,7}$]decane(adamantane). The monocyclic, bicyclic, and tricyclic cycloalkyls can be unsubstituted or substituted, and are attached to the parent molecular moiety through any substitutable atom contained within the ring system.

The term "cycloalkenyl" or "cycloalkene" as used herein, means a monocyclic or a bicyclic hydrocarbon ring system. The monocyclic cycloalkenyl has four-, five-, six-, seven- or eight carbon atoms and zero heteroatoms. The four-membered ring systems have one double bond, the five-or six-membered ring systems have one or two double bonds, and the seven- or eight-membered ring systems have one, two or three double bonds. Representative examples of monocyclic cycloalkenyl groups include, but are not limited to, cyclobutenyl, cyclopentenyl, cyclohexenyl, cycloheptenyl and cyclooctenyl. The bicyclic cycloalkenyl is a monocyclic cycloalkenyl fused to a monocyclic cycloalkyl group, or a monocyclic cycloalkenyl fused to a monocyclic cycloalkenyl group. The monocyclic or bicyclic cycloalkenyl ring may contain one or two alkylene bridges, each consisting of one, two or three carbon atoms, each linking two non-adjacent carbon atoms of the ring system. Representative examples of the bicyclic cycloalkenyl groups include, but are not limited to, 4,5,6,7-tetrahydro-3aH-indene, octahydronaphthalenyl and 1,6-dihydro-pentalene. The monocyclic and bicyclic cycloalkenyl can be attached to the parent molecular moiety through any substitutable atom contained within the ring systems, and can be unsubstituted or substituted.

The term "halo" or "halogen" as used herein, means Cl, Br, I, or F.

The term "haloalkyl" as used herein, means an alkyl group, as defined herein, in which one, two, three, four, five or six hydrogen atoms are replaced by halogen. Representative examples of haloalkyl include, but are not limited to, chloromethyl, 2-fluoroethyl, 2,2,2-trifluoroethyl, trifluoromethyl, difluoromethyl, pentafluoroethyl, 2-chloro-3-fluoropentyl, and trifluoropropyl such as 3,3,3-trifluoropropyl.

The term "heterocycle" or "heterocyclic" as used herein, means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, thiazolinyl, thiazolidinyl, thiomorpholinyl, 1,1-dioxidothiomorpholinyl(thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a bridged monocyclic heterocycle ring system in which two non adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 2,3-dihydrobenzothienyl, azabicyclo[2.2.1]heptyl (including 2-azabicyclo[2.2.1]hept-2-yl), 2,3-dihydro-1H-indolyl, isoindolinyl, octahydrocyclopenta[c]pyrrolyl, octahydropyrrolopyridinyl, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but not limited to, octahydro-2,5-epoxypentalene, hexahydro-2H-2,5-methanocyclopenta[b]furan, hexahydro-1H-1,4-methanocyclopenta[c]furan, aza-adamantane(1-azatricyclo[3.3.1.1$^{3,7}$]decane), and oxa-adamantane (2-oxatricyclo[3.3.1.1$^{3,7}$]decane). The monocyclic, bicyclic, and tricyclic heterocycles are connected to the parent molecular moiety through any carbon atom or any nitrogen atom contained within the rings, and can be unsubstituted or substituted.

The term "heteroaryl" as used herein, means a monocyclic heteroaryl or a bicyclic heteroaryl. The monocyclic heteroaryl is a five- or six-membered ring. The five-membered ring contains two double bonds. The five-membered ring may contain one heteroatom selected from O or S; or one, two, three, or four nitrogen atoms and optionally one oxygen or sulfur atom. The six-membered ring contains three double bonds and one, two, three or four nitrogen atoms. Representative examples of monocyclic heteroaryl include, but are not limited to, furanyl, imidazolyl, isoxazolyl, isothiazolyl, oxadiazolyl, 1,3-oxazolyl, pyridinyl, pyridazinyl, pyrimidinyl, pyrazinyl, pyrazolyl, pyrrolyl, tetrazolyl, thiadiazolyl, 1,3-thiazolyl, thienyl, triazolyl, and triazinyl. The bicyclic heteroaryl consists of a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Representative examples of bicyclic heteroaryl groups include, but are not limited to, benzofuranyl, benzothienyl, benzoxazolyl, benzimidazolyl, benzoxadiazolyl, 6,7-dihydro-1,3-benzothiazolyl, benzotriazolyl, imidazo[1,2-a]pyridinyl, indazolyl, indolyl, isoindolyl, isoquinolinyl, naphthyridinyl, pyridoimidazolyl, quinolinyl, thiazolo[5,4-b]pyridin-2-yl, thiazolo[5,4-d]pyrimidin-2-yl, and 5,6,7,8- tetrahydroquinolin-5-yl. The monocyclic and bicyclic heteroaryl groups of the present invention can be substituted or unsubstituted and are connected to the parent molecular moiety through any carbon atom or any nitrogen atom contained within the ring systems.

The term "heteroatom" as used herein, means a nitrogen, oxygen, or sulfur atom.

The term "hydroxyl" or "hydroxy" as used herein, means an —OH group.

The term "oxo" as used herein, means a =O group.

b. Compounds

Compounds of the invention have the formula (I) as described above.

Particular values of variable groups in compounds of formula (I) are as follows. Such values may be used where appropriate with any of the other values, definitions, claims or embodiments defined hereinbefore or hereinafter.

More particularly, compounds of formula (I) can include, but are not limited to compounds wherein X is $CH_2$, NC(O)OtBu, NH, or N-alkyl, O or S(O), wherein r is 0, 1, or 2.

In one embodiment, X is $CH_2$.
In another embodiment, X is NC(O)OtBu.
In another embodiment, X is NH.
In another embodiment, X is O.
In another embodiment, X is S.
In another embodiment, X is S(O).
In a further embodiment, X is $S(O)_2$.
In one embodiment, n is 1 or 2.
In another embodiment, n is 1.
In a further embodiment, n is 2.
In one embodiment, X is $CH_2$ and n is 1.
In another embodiment, X is NC(O)OtBu and n is 1.
In another embodiment, X is NH and n is 1.
In another embodiment, X is O and n is 1.
In another embodiment, X is S and n is 1.
In another embodiment, X is S(O) and n is 1.
In a further embodiment, X is $S(O)_2$ and n is 1.
In one embodiment, X is $CH_2$ and n is 2.
In another embodiment, X is NC(O)OtBu and n is 2.
In another embodiment, X is NH and n is 2.
In another embodiment, X is O and n is 2.
In another embodiment, X is S and n is 2.
In another embodiment, X is S(O) and n is 2.
In a further embodiment, X is $S(O)_2$ and n is 2.

In one embodiment, $Ar^1$ is heteroaryl; wherein $Ar^1$ is unsubstituted or further substituted with 1, 2, 3, 4, or 5 substituents independently selected from the group consisting of alkyl, alkenyl, alkynyl, halogen, —CN, —$NO_2$, —$OR^a$, —$S(R^c)$, —$S(O)(R^c)$, —$S(O)_2R^c$, —$S(O)_2N(R^b)_2$, —$C(O)R^b$, —$C(O)O(R^b)$, —$C(O)N(R^b)_2$, —$N(R^b)_2$, —$N(R^b)C(O)R^b$, —$N(R^b)C(O)O(R^b)$, —$N(R^b)S(O)_2R^c$, haloalkyl, —$(CR^dR^e)_m$—$OR^a$, —$(CR^dR^e)_m$—$S(R^c)$, —$(CR^dR^e)_m$—$S(O)(R^c)$, —$(CR^dR^e)_m$—$S(O)_2R^c$, —$(CR^dR^e)_m$—$S(O)_2N(R^b)_2$, —$(CR^dR^e)_m$—$C(O)R^b$, —$(CR^dR^e)_m$—$C(O)O(R^b)$, —$(CR^dR^e)_m$—$C(O)N(R^b)_2$, —$(CR^dR^e)_m$—$N(R^b)_2$, —$(CR^dR^e)_m$—$N(R^b)C(O)R^b$, —$(CR^dR^e)_m$—$N(R^b)C(O)O(R^b)$, and —$(CR^dR^e)_m$—$N(R^b)S(O)_2R^c$; wherein, $R^a$, at each occurrence, is independently hydrogen, alkyl, haloalkyl, or —$(CR^dR^e)_m$—O(alkyl); wherein, $R^b$, at each occurrence, is independently hydrogen, alkyl, haloalkyl, or $G^1$; wherein, $R^c$, at each occurrence, is independently alkyl or haloalkyl; wherein, $R^d$ and $R^e$, at each occurrence, are each independently hydrogen, halogen, alkyl, or haloalkyl; and m, at each occurrence, is independently 1, 2, 3, 4, 5, or 6.

In another embodiment, $Ar^1$ is aryl; wherein $Ar^1$ is unsubstituted or further substituted with 1, 2, 3, 4, or 5 substituents independently selected from the group consisting of alkyl, alkenyl, alkynyl, halogen, —CN, —$NO_2$, —$OR^a$, —$S(R^c)$, —$S(O)(R^c)$, —$S(O)_2R^c$, —$S(O)_2N(R^b)_2$, —$C(O)R^b$, —$C(O)O(R^b)$, —$C(O)N(R^b)_2$, —$N(R^b)_2$, —$N(R^b)C(O)R^b$, —$N(R^b)C(O)O(R^b)$, —$N(R^b)S(O)_2R^c$, haloalkyl, —$(CR^dR^e)_m$—$OR^a$, —$(CR^dR^e)_m$—$S(R^c)$, —$(CR^dR^e)_m$—$S(O)(R^c)$, —$(CR^dR^e)_m$—$S(O)_2R^c$, —$(CR^dR^e)_m$—$S(O)_2N(R^b)_2$, —$(CR^dR^e)_m$—$C(O)R^b$, —$(CR^dR^e)_m$—$C(O)O(R^b)$, —$(CR^dR^e)_m$—$C(O)N(R^b)_2$, —$(CR^dR^e)_m$—$N(R^b)_2$, —$(CR^dR^e)_m$—$N(R^b)C(O)R^b$, —$(CR^dR^e)_m$—$N(R^b)C(O)O(R^b)$, and —$(CR^dR^e)_m$—$N(R^b)S(O)_2R^c$; wherein, $R^a$, at each occurrence, is independently hydrogen, alkyl, haloalkyl, or —$(CR^dR^e)_m$—O(alkyl); wherein, $R^b$, at each occurrence, is independently hydrogen, alkyl, haloalkyl, or $G^1$; wherein, $R^c$, at each occurrence, is independently alkyl or haloalkyl; wherein, $R^d$ and $R^e$, at each occurrence, are each independently hydrogen, halogen, alkyl, or haloalkyl; and m, at each occurrence, is independently 1, 2, 3, 4, 5, or 6.

In another embodiment, $Ar^1$ is phenyl; wherein $Ar^1$ is unsubstituted or further substituted with 1, 2, or 3 substituents independently selected from the group consisting of alkyl or halogen.

In a further embodiment, $Ar^1$ is phenyl; wherein $Ar^1$ is unsubstituted or further substituted with 1 halogen substituent In one embodiment, $R^1$ is hydrogen, alkyl, or $G^1$.
In another embodiment, $R^1$ is hydrogen.
In another embodiment, $R^1$ is alkyl.
In a further embodiment, $R^1$ is $G^1$.

In one embodiment, $G^1$, at each occurrence, is independently aryl, heteroaryl, heterocycle, cycloalkyl, or cycloalkenyl; wherein each $G^1$ is independently unsubstituted or further substituted with 1, 2, 3, 4, 5, or 6 substituents independently selected from the group consisting of alkyl, alkenyl, alkynyl, halogen, oxo, —CN, —$NO_2$, —$OR^a$, —$S(R^c)$, —$S(O)(R^c)$, —$S(O)_2R^c$, —$S(O)_2N(R^b)_2$, $C(O)R^b$, —$C(O)O(R^b)$, —$C(O)N(R^b)_2$, —$N(R^b)_2$, —$N(R^b)C(O)R^b$, —$N(R^b)C(O)O(R^b)$, —$N(R^b)S(O)_2R^c$, haloalkyl, —$(CR^dR^e)_m$—$OR^a$, —$(CR^dR^e)_m$—$S(R^c)$, —$(CR^dR^e)_m$—$S(O)(R^c)$, —$(CR^dR^e)_m$—$S(O)_2R^c$, —$(CR^dR^e)_m$—$S(O)_2N(R^b)_2$, —$(CR^dR^e)_m$—$C(O)R^b$, —$(CR^dR^e)_m$—$C(O)O(R^b)$, —$(CR^dR^e)_m$—$C(O)N(R^b)_2$, —$(CR^dR^e)_m$—$N(R^b)_2$, —$(CR^dR^e)_m$—$N(R^b)C(O)R^b$, —$(CR^dR^e)_m$—$N(R^b)C(O)O(R^b)$, and —$(CR^dR^e)_m$—$N(R^b)S(O)_2R^c$; wherein, $R^a$, at each occurrence, is independently hydrogen, alkyl, haloalkyl, or —$(CR^dR^e)_m$—O(alkyl); wherein, $R^b$, at each occurrence, is independently hydrogen, alkyl, haloalkyl, or $G^1$; wherein, $R^c$, at each occurrence, is independently alkyl or haloalkyl; wherein, $R^d$ and $R^e$, at each occurrence, are each independently hydrogen, halogen, alkyl, or haloalkyl; and m, at each occurrence, is independently 1, 2, 3, 4, 5, or 6.

In another embodiment, $G^1$, at each occurrence, is heteroaryl; wherein each $G^1$ is independently unsubstituted or further substituted with 1, 2, 3, 4, 5, or 6 substituents independently selected from the group consisting of alkyl, alkenyl, alkynyl, halogen, —CN, —$NO_2$, —$OR^a$, —$S(R^c)$, —$S(O)(R^c)$, —$S(O)_2R^c$, —$S(O)_2N(R^b)_2$, $C(O)R^b$, —$C(O)O(R^b)$, —$C(O)N(R^b)_2$, —$N(R^b)_2$, —$N(R^b)C(O)R^b$, —$N(R^b)C(O)O(R^b)$, —$N(R^b)S(O)_2R^c$, haloalkyl, —$(CR^dR^e)_m$—$OR^a$, —$(CR^dR^e)_m$—$S(R^c)$, —$(CR^dR^e)_m$—$S(O)(R^c)$, —$(CR^dR^e)_m$—$S(O)_2R^c$, —$(CR^dR^e)_m$—$S(O)_2N(R^b)_2$, —$(CR^dR^e)_m$—$C(O)R^b$, —$(CR^dR^e)_m$—$C(O)O(R^b)$, —$(CR^dR^e)_m$—$C(O)N(R^b)_2$, —$(CR^dR^e)_m$—$N(R^b)_2$, —$(CR^dR^e)_m$—$N(R^b)C(O)R^b$, —$(CR^dR^e)_m$—$N(R^b)C(O)O(R^b)$, and —$(CR^dR^e)_m$—$N(R^b)S(O)_2R^c$; wherein, $R^a$, at each occurrence, is independently hydrogen, alkyl, haloalkyl, or —$(CR^dR^e)_m$—O(alkyl); wherein, $R^b$, at each occurrence, is independently hydrogen, alkyl, haloalkyl, or $G^1$; wherein, $R^c$, at each occurrence, is independently alkyl or haloalkyl; wherein, $R^d$ and $R^e$, at each occurrence, are each independently hydrogen, halogen, alkyl, or haloalkyl; and m, at each occurrence, is independently 1, 2, 3, 4, 5, or 6.

In another embodiment, $G^1$, at each occurrence, is independently heterocycle; wherein each $G^1$ is independently unsubstituted or further substituted with 1, 2, 3, 4, 5, or 6 substituents independently selected from the group consisting of alkyl, alkenyl, alkynyl, halogen, oxo, —CN, —NO$_2$, —OR$^a$, —S(R$^c$), —S(O)(R$^c$), —S(O)$_2$R$^c$, —S(O)$_2$N(R$^b$)$_2$, C(O)R$^b$, —C(O)O(R$^b$), —C(O)N(R$^b$)$_2$, —N(R$^b$)$_2$, —N(R$^b$)C(O)R$^b$, —N(R$^b$)C(O)O(R$^b$), —N(R$^b$)S(O)$_2$R$^c$, haloalkyl, —(CR$^d$R$^e$)$_m$—OR$^a$, —(CR$^d$R$^e$)$_m$—S(R$^c$), —(CR$^d$R$^e$)$_m$—S(O)(R$^c$), —(CR$^d$R$^e$)$_m$—S(O)$_2$R$^c$, —(CR$^d$R$^e$)$_m$—S(O)$_2$N(R$^b$)$_2$, —(CR$^d$R$^e$)$_m$—C(O)R$^b$, —(CR$^d$R$^e$)$_m$—C(O)O(R$^b$), —(CR$^d$R$^e$)$_m$—C(O)N(R$^b$)$_2$, —(CR$^d$R$^e$)$_m$—N(R$^b$)$_2$, —(CR$^d$R$^e$)$_m$—N(R$^b$)C(O)R$^b$, —(CR$^d$R$^e$)$_m$—N(R$^b$)C(O)O(R$^b$), and —(CR$^d$R$^e$)$_m$—N(R$^b$)S(O)$_2$R$^c$; wherein, $R^a$, at each occurrence, is independently hydrogen, alkyl, haloalkyl, or —(CR$^d$R$^e$)$_m$—O(alkyl); wherein, $R^b$, at each occurrence, is independently hydrogen, alkyl, haloalkyl, or $G^1$; wherein, $R^c$, at each occurrence, is independently alkyl or haloalkyl; wherein, $R^d$ and $R^e$, at each occurrence, are each independently hydrogen, halogen, alkyl, or haloalkyl; and m, at each occurrence, is independently 1, 2, 3, 4, 5, or 6.

In another embodiment, $G^1$, at each occurrence, is cycloalkyl; wherein each $G^1$ is independently unsubstituted or further substituted with 1, 2, 3, 4, 5, or 6 substituents independently selected from the group consisting of alkyl, alkenyl, alkynyl, halogen, oxo, —CN, —NO$_2$, —OR$^a$, —S(R$^c$), —S(O)(R$^c$), —S(O)$_2$R$^c$, —S(O)$_2$N(R$^b$)$_2$, C(O)R$^b$, —C(O)O(R$^b$), —C(O)N(R$^b$)$_2$, —N(R$^b$)$_2$, —N(R$^b$)C(O)R$^b$, —N(R$^b$)C(O)O(R$^b$), —N(R$^b$)S(O)$_2$R$^c$, haloalkyl, —(CR$^d$R$^e$)$_m$—OR$^a$, —(CR$^d$R$^e$)$_m$—S(R$^c$), —(CR$^d$R$^e$)$_m$—S(O)(R$^c$), —(CR$^d$R$^e$)$_m$—S(O)$_2$R$^c$, —(CR$^d$R$^e$)$_m$—S(O)$_2$N(R$^b$)$_2$, —(CR$^d$R$^e$)$_m$—C(O)R$^b$, —(CR$^d$R$^e$)$_m$—C(O)O(R$^b$), —(CR$^d$R$^e$)$_m$—C(O)N(R$^b$)$_2$, —(CR$^d$R$^e$)$_m$—N(R$^b$)$_2$, —(CR$^d$R$^e$)$_m$—N(R$^b$)C(O)R$^b$, —(CR$^d$R$^e$)$_m$—N(R$^b$)C(O)O(R$^b$), and —(CR$^d$R$^e$)$_m$—N(R$^b$)S(O)$_2$R$^c$; wherein, $R^a$, at each occurrence, is independently hydrogen, alkyl, haloalkyl, or —(CR$^d$R$^e$)$_m$—O(alkyl); wherein, $R^b$, at each occurrence, is independently hydrogen, alkyl, haloalkyl, or $G^1$; wherein, $R^c$, at each occurrence, is independently alkyl or haloalkyl; wherein, $R^d$ and $R^e$, at each occurrence, are each independently hydrogen, halogen, alkyl, or haloalkyl; and m, at each occurrence, is independently 1, 2, 3, 4, 5, or 6.

In another embodiment, $G^1$, at each occurrence, is independently cycloalkenyl; wherein each $G^1$ is independently unsubstituted or further substituted with 1, 2, 3, 4, 5, or 6 substituents independently selected from the group consisting of alkyl, alkenyl, alkynyl, halogen, oxo, —CN, —NO$_2$, —OR$^a$, —S(R$^c$), —S(O)(R$^c$), —S(O)$_2$R$^c$, —S(O)$_2$N(R$^b$)$_2$, C(O)R$^b$, —C(O)O(R$^b$), —C(O)N(R$^b$)$_2$, —N(R$^b$)$_2$, —N(R$^b$)C(O)R$^b$, —N(R$^b$)C(O)O(R$^b$), —N(R$^b$)S(O)$_2$R$^c$, haloalkyl, —(CR$^d$R$^e$)$_m$—OR$^a$, —(CR$^d$R$^e$)$_m$—S(R$^c$), —(CR$^d$R$^e$)$_m$—S(O)(R$^c$), —(CR$^d$R$^e$)$_m$—S(O)$_2$R$^c$, —(CR$^d$R$^e$)$_m$—S(O)$_2$N(R$^b$)$_2$, —(CR$^d$R$^e$)$_m$—C(O)R$^b$, —(CR$^d$R$^e$)$_m$—C(O)O(R$^b$), —(CR$^d$R$^e$)$_m$—C(O)N(R$^b$)$_2$, —(CR$^d$R$^e$)$_m$—N(R$^b$)$_2$, —(CR$^d$R$^e$)$_m$—N(R$^b$)C(O)R$^b$, —(CR$^d$R$^e$)$_m$—N(R$^b$)C(O)O(R$^b$), and —(CR$^d$R$^e$)$_m$—N(R$^b$)S(O)$_2$R$^c$; wherein, $R^a$, at each occurrence, is independently hydrogen, alkyl, haloalkyl, or —(CR$^d$R$^e$)$_m$—O(alkyl); wherein, $R^b$, at each occurrence, is independently hydrogen, alkyl, haloalkyl, or $G^1$; wherein, $R^c$, at each occurrence, is independently alkyl or haloalkyl; wherein, $R^d$ and $R^e$, at each occurrence, are each independently hydrogen, halogen, alkyl, or haloalkyl; and m, at each occurrence, is independently 1, 2, 3, 4, 5, or 6.

In a further embodiment, $G^1$, at each occurrence, is independently aryl; wherein each $G^1$ is independently unsubstituted or further substituted with 1, 2, 3, 4, 5, or 6 substituents independently selected from the group consisting of alkyl, alkenyl, alkynyl, halogen, —CN, —NO$_2$, —OR$^a$, —S(R$^c$), —S(O)(R$^c$), —S(O)$_2$R$^c$, —S(O)$_2$N(R$^b$)$_2$, C(O)R$^b$, —C(O)O(R$^b$), —C(O)N(R$^b$)$_2$, —N(R$^b$)$_2$, —N(R$^b$)C(O)R$^b$, —N(R$^b$)C(O)O(R$^b$), —N(R$^b$)S(O)$_2$R$^c$, haloalkyl, —(CR$^d$R$^e$)$_m$—OR$^a$, —(CR$^d$R$^e$)$_m$—S(R$^c$), —(CR$^d$R$^e$)$_m$—S(O)(R$^c$), —(CR$^d$R$^e$)$_m$—S(O)$_2$R$^c$, —(CR$^d$R$^e$)$_m$—S(O)$_2$N(R$^b$)$_2$, —(CR$^d$R$^e$)$_m$—C(O)R$^b$, —(CR$^d$R$^e$)$_m$—C(O)O(R$^b$), —(CR$^d$R$^e$)$_m$—C(O)N(R$^b$)$_2$, —(CR$^d$R$^e$)$_m$—N(R$^b$)$_2$, —(CR$^d$R$^e$)$_m$—N(R$^b$)C(O)R$^b$, —(CR$^d$R$^e$)$_m$—N(R$^b$)C(O)O(R$^b$), and —(CR$^d$R$^e$)$_m$—N(R$^b$)S(O)$_2$R$^c$; wherein, $R^a$, at each occurrence, is independently hydrogen, alkyl, haloalkyl, or —(CR$^d$R$^e$)$_m$—O(alkyl); wherein, $R^b$, at each occurrence, is independently hydrogen, alkyl, haloalkyl, or $G^1$; wherein, $R^c$, at each occurrence, is independently alkyl or haloalkyl; wherein, $R^d$ and $R^e$, at each occurrence, are each independently hydrogen, halogen, alkyl, or haloalkyl; and m, at each occurrence, is independently 1, 2, 3, 4, 5, or 6.

In one embodiment, $R^1$ is $G^1$, wherein $G^1$ is phenyl unsubstituted or further substituted with 1 halogen.

In one embodiment, Y is (i), (ii), (iii), (iv), (v), (vi), (vii), (viii), (ix), (x) or (xi);

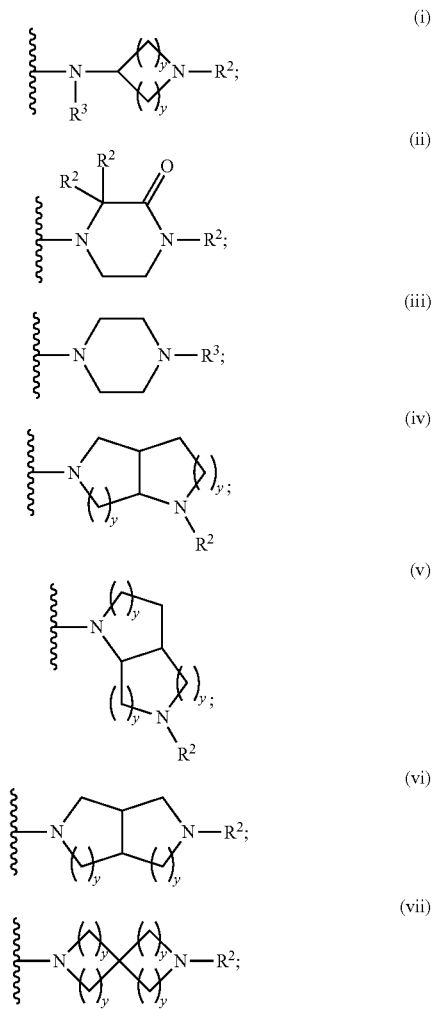

-continued

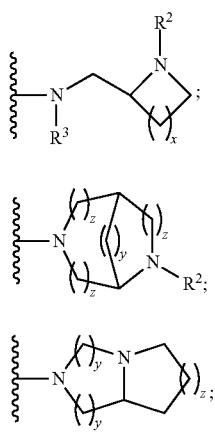

(viii)

(ix)

(x)

(xi)

wherein x is 1, 2, or 3; wherein y at each occurrence, is independently 1 or 2; wherein z at each occurrence, is independently 0, 1, or 2; wherein Q is O, S, or CH$_2$; wherein R$^2$, at each occurrence, is independently hydrogen or alkyl; and wherein R$^3$ is hydrogen, alkyl, or G$^1$.

In one embodiment, (i) is (i-a), (i-b), (i-c), (i-d), or (i-e).

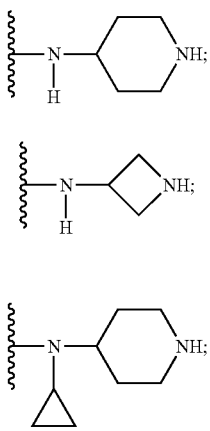

(i-a)

(i-b)

(i-c)

(i-d)

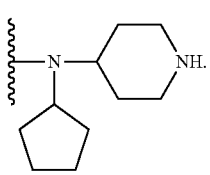

(i-e)

In one embodiment, (ii) is (ii-a) or (ii-b).

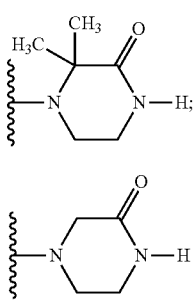

(ii-a)

(ii-b)

In one embodiment, (iii) is (iii-a), (iii-b), or (iii-c).

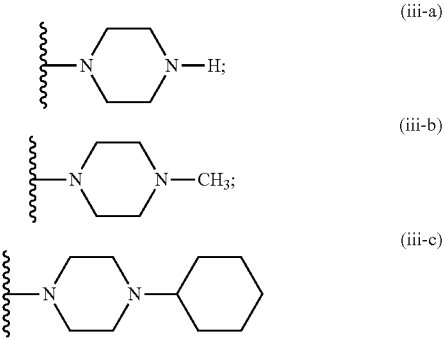

(iii-a)

(iii-b)

(iii-c)

In one embodiment, (iv) is (iv-a) or (iv-b).

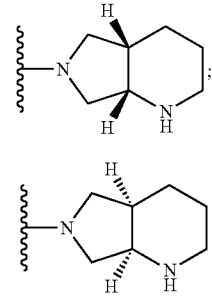

(iv-a)

(iv-b)

In one embodiment, (v) is (v-a) or (v-b).

(v-a)

(v-b)

In one embodiment, (vi) is (vi-a).

(vi-a)

In one embodiment, (vii) is (vii-a).

(vii-a)

In one embodiment, (viii) is (viii-a) or (viii-b).

(viii-a)

(viii-b)

In one embodiment, (ix) is (ix-a).

(ix-a)

In one embodiment. (x) is (x-a) or (x-b).

(x-a)

(x-b)

In one embodiment, (xi) is (xi-a), (xi-b), or (xi-c).

(xi-a)

(xi-b)

(xi-c)

In one embodiment, X is $CH_2$, n is 2, $Ar^1$ and $R^1$ are each phenyl unsubstituted or substituted with 1 halogen, and Y is (i-a), (i-b), (ii-a), (ii-b), (iii-a), (iii-b), (iv-a), (iv-b), (v-b), (vi-a), (vii-a), (viii-a), (viii-b), or (ix-a).

In another embodiment, X is $CH_2$, n is 1, $Ar^1$ and $R^1$ are each phenyl unsubstituted or substituted with 1 halogen, and Y is (i-b), (i-c), (i-d), (i-e), (iii-a), (iii-c), (vii-a), or (x-a).

Specific embodiments of compounds contemplated as part of the invention include, but are not limited to:

2-(2-oxo-3,3-diphenylpiperidin-1-yl)-N-piperidin-4-ylacetamide;

3,3-dimethyl-4-[(2-oxo-3,3-diphenylpiperidin-1-yl)acetyl]piperazin-2-one;

1-{2-[(4aS,7aS)-octahydro-6H-pyrrolo[3,4-b]pyridin-6-yl]-2-oxoethyl}-3,3-diphenylpiperidin-2-one;

1-{2-[(4aR,7aR)-octahydro-6H-pyrrolo[3,4-b]pyridin-6-yl]-2-oxoethyl}-3,3-diphenylpiperidin-2-one;

1-{2-[(4aS,7aS)-octahydro-1H-pyrrolo[3,4-b]pyridin-1-yl]-2-oxoethyl}-3,3-diphenylpiperidin-2-one;

1-(2-hexahydropyrrolo[3,4-c]pyrrol-2(1H)-yl-2-oxoethyl)-3,3-diphenylpiperidin-2-one;

1-[2-(2,7-diazaspiro[3.5]non-2-yl)-2-oxoethyl]-3,3-diphenylpiperidin-2-one;

2-(2-oxo-3,3-diphenylpiperidin-1-yl)-N-[(2R)-pyrrolidin-2-ylmethyl]acetamide;

2-(2-oxo-3,3-diphenylpiperidin-1-yl)-N-[(2S)-pyrrolidin-2-ylmethyl]acetamide;

4-[(2-oxo-3,3-diphenylpiperidin-1-yl)acetyl]piperazin-2-one;

N-azetidin-3-yl-2-(2-oxo-3,3-diphenylpiperidin-1-yl)acetamide;

1-(2-oxo-2-piperazin-1-ylethyl)-3,3-diphenylpiperidin-2-one;

1-{2-[(1S*,5S*)-3,6-diazabicyclo[3.2.1]oct-3-yl]-2-oxoethyl}-3,3-diphenylpiperidin-2-one;

3,3-bis(4-fluorophenyl)-1-(2-oxo-2-piperazin-1-ylethyl)pyrrolidin-2-one;

3,3-bis(4-fluorophenyl)-1-{2-[(8aR)-hexahydropyrrolo[1,2-a]pyrazin-2(1H)-yl]-2-oxoethyl}pyrrolidin-2-one;

N-azetidin-3-yl-2-[3,3-bis(4-fluorophenyl)-2-oxopyrrolidin-1-yl]acetamide;

2-[3,3-bis(4-fluorophenyl)-2-oxopyrrolidin-1-yl]-N-cyclopropyl-N-piperidin-4-ylacetamide;

2-[3,3-bis(4-fluorophenyl)-2-oxopyrrolidin-1-yl]-N-cyclobutyl-N-piperidin-4-ylacetamide;

2-[3,3-bis(4-fluorophenyl)-2-oxopyrrolidin-1-yl]-N-cyclopentyl-N-piperidin-4-ylacetamide;

1-[2-(2,7-diazaspiro[3.5]non-2-yl)-2-oxoethyl]-3,3-bis(4-fluorophenyl)pyrrolidin-2-one;

1-[2-(4-cyclohexylpiperazin-1-yl)-2-oxoethyl]-3,3-diphenylpyrrolidin-2-one;

1-[2-(4-methylpiperazin-1-yl)-2-oxoethyl]-3,3-diphenylpiperidin-2-one;

3,3-bis(4-fluorophenyl)-1-(2-oxo-2-piperazin-1-ylethyl)piperidin-2-one;

1-(2-oxo-2-piperazin-1-ylethyl)-3,3-diphenylpyrrolidin-2-one; or 3,3-bis(4-chlorophenyl)-1-(2-oxo-2-piperazin-1-ylethyl)pyrrolidin-2-one.

Compounds of the present application may exist as stereoisomers wherein, asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, Pure Appl. Chem., 1976, 45: 13-30.

On occasion, the relative stereochemistry of an enantiomeric pair is known, however, the absolute configuration is not known. In that circumstance, the relative stereochemistry descriptor terms "R*" and "S*" are used. The terms "R*" and "S*" used herein are defined in Eliel, E. L.; Wilen, S. H. Stereochemistry of Organic Compounds; John Wiley & Sons, Inc.: New York, 1994; pp 119-120 and 1206.

The present application contemplates various stereoisomers and mixtures thereof and these are specifically included within the scope of this application. Stereoisomers include enantiomers and diastereomers, and mixtures of enantiomers or diastereomers. Individual stereoisomers of compounds of the present application may be prepared synthetically from commercially available starting materials which contain asymmetric or chiral centers or by preparation of racemic mixtures followed by resolution which is well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

Geometric isomers may exist in the present compounds. The invention contemplates the various geometric isomers and mixtures thereof resulting from the disposition of substituents around a carbon-carbon double bond, a carbon-nitrogen double bond, a cycloalkyl group, or a heterocycle group. Substituents around a carbon-carbon double bond or a carbon-nitrogen bond are designated as being of Z or E configuration and substituents around a cycloalkyl or a heterocycle are designated as being of cis or trans configuration.

Within the present invention it is to be understood that compounds disclosed herein may exhibit the phenomenon of tautomerism.

Thus, the formulae drawings within this specification can represent only one of the possible tautomeric or stereoisomeric forms. It is to be understood that the invention encompasses any tautomeric or stereoisomeric form, and mixtures thereof, and is not to be limited merely to any one tautomeric or stereoisomeric form utilized within the naming of the compounds or formulae drawings.

Compounds of this invention can exist in an isotopic form containing one or more atoms having an atomic mass or mass number different from the atomic mass or mass number most abundantly found in nature. Isotopes of atoms such as hydrogen, carbon, phosphorous, sulfur fluorine, chlorine, and iodine include, but are not limited to $^2H$, $^3H$, $^{11}C$, $^{14}C$, $^{32}P$, $^{35}S$, $^{18}F$, $^{36}Cl$, and $^{125}I$, respectively. Compounds that contain other isotopes of these and/or other atoms are within the scope of this invention. Compounds containing tritium ($^3H$) and $^{14}C$ radioisotopes are preferred in general for their ease in preparation and detectability for radiolabeled compounds. Isotopically labeled compounds of this invention can be prepared by the general methods well known to persons having ordinary skill in the art. Such Isotopically labeled compounds can be conveniently prepared by carrying out the procedures disclosed in the Examples and Schemes below by substituting a readily available isotopically labeled reagent for a non-isotopically labeled reagent.

c. Biological Data

Abbreviations which have been used in the descriptions of Biological Data that follow are: EDTA for ethylenediaminetetraacetic acid; EGTA for ethylene glycol tetraacetic acid; FBS for fetal bovine serum; FLIPR for fluorometric imaging plate reader; HBSS for Hank's balanced salt solution; HEPES for 4-(2-hydroxyethyl)-1-piperazineethanesulfonic acid; i.p. for intraperitoneal; MEM for minimum essential medium; MEM NEAA for minimum essential medium non-essential amino acid; $Mg_2ATP$ for dimagnesium adenosine triphosphate complex; p.o. for per orem (by mouth); and TEA-Cl for tetraethylammonium chloride.

(i) In Vitro Methods—Assessment of Calcium Channel Activity Using FLIPR

IMR32 cells endogenously expressing human $Ca_v2.2$ were assayed for $Ca^{2+}$ influx using a no-wash calcium indicator dye (Calcium 4 dye: Molecular Probes) and FLIPR technology (Lubin, M L; et al. Assay and Drug Development Technologies 2006; 4: 689-694). The IMR32 cells were maintained in MEM media containing 10% (v/v) FBS, 1% (v/v) antibiotic/antimitotic, 1% (v/v) sodium pyruvate and 1% (v/v) MEM NEAA. Following dissociation in 0.05% (v/v) trypsin/EDTA, cells were seeded into black 1×96-well plates (Corning Cellbind) at a density of $1\text{-}1.2\times10^5$ cells/well and incubated in the maintenance media above for 48 hours at 37° C. Immediately prior to performing the assay the media was removed and cells were loaded for 1.5 hours with 1× Calcium 4 dye prepared in HBSS (137 mM NaCl, 5.4 mM KCl, 0.25 mM $Na_2HPO_4$, 0.44 mM $KH_2PO_4$, 1.3 mM $CaCl_2$, 1 mM $MgSO_4$, 4.2 mM $NaHCO_3$) containing HEPES pH 7.4 at room temperature. After dye loading and a subsequent 60 minute pre-incubation with compounds (full log dilutions from 10 μM to 0.1 nM) in the presence of 1.3 mM $CaCl_2$ and 2 μM nifedipine to block endogenous L-type channels, the external $Ca^{2+}$ concentration was increased to 5 mM $CaCl_2$ and the cells concomitantly depolarized with 80 mM KCl to assay channel activity. To determine the $IC_{50}$ values, the percent inhibition of the compound at each concentration was determined relative to the activity in the absence of inhibitor, and data was fitted using non-linear regression sigmoidal dose response curve analysis with GraphPad Prism®.

Table 1 lists $IC_{50}$ values for compounds of the present invention.

TABLE 1

FLIPR Assessment for Human Cav2.2 Channels

| Example | $IC_{50}$ (μM) |
|---|---|
| 1 | >30 |
| 2 | >30 |
| 3 | 10.1 |
| 4 | 11.8 |
| 5 | 13.5 |
| 6 | >30 |
| 7 | >30 |
| 8 | >9 |
| 9 | >30 |
| 10 | >30 |
| 11 | >30 |
| 12 | 15.0 |
| 13 | 9.78 |
| 14 | 9.22 |
| 15 | 12.9 |
| 16 | 5.54 |

TABLE 1-continued

FLIPR Assessment for Human Cav2.2 Channels

| Example | IC$_{50}$ (µM) |
|---|---|
| 17 | 12.9 |
| 18 | 5.06 |
| 19 | 4.30 |
| 20 | 13.1 |
| 21 | 3.86 |
| 22 | >30 |
| 23 | 2.96 |
| 24 | 16.4 |
| 25 | 8.89 |

(ii) In Vitro Methods—Electrophysiologic Assessment of Calcium Channel Activity

Patch-clamp recordings were performed using HEK293 cells stably expressing hCa$_v$3.2. Cells were plated in T175 flasks and grown at 37° C. and under 5% $CO_2$ to approximately 50% confluency. On the day of the experiment, cells were harvested with Detachin™ cell detachment solution (Genlantis, San Diego, Calif.) and maintained in serum-free culture medium supplemented with 25 mM HEPES up to several hours prior to experiment. Whole-cell patch-clamp recordings were obtained using extracellular saline consisting of (mM): 87.5 CsCl, 40 TEA-Cl, 5 $CaCl_2$, 1 $MgCl_2$, 10 HEPES, 10 glucose. The pH was adjusted to 7.2 with CsOH and the osmolarity was adjusted to approximately 310 mOsm with sucrose. Intracellular solution consisted of (mM): 112 CsCl, 27 CsF, 2 NaCl, 8.2 EGTA, 10 HEPES. Prior to an experiment 4 mM $Mg_2ATP$ was added and the pH was adjusted to 7.2 with CsOH with an osmolarity of approximately 290 mOsm. A two-pulse voltage protocol was utilized to assess compound inhibition. First, cells were held with an 8 second pre-pulse at −100 mV prior to a 160 millisecond test pulse to −30 mV. This was followed by an 8 second pre-pulse at approximately −75 mV prior to a 160 mV test pulse to −30 mV. Increasing concentrations of antagonist were applied to individual cells in a multi-addition format with 5 minutes in each test concentration. For each cell, responses were normalized to dimethyl sulfoxide vehicle control to generate concentration-response curves.

Table 2 lists IC$_{50}$ values for compounds of the present invention.

TABLE 2

Electrophysiologic Assessment for Human Cav3.2 Channels

| Example | Human Ca$_v$3.2<br>−77 mV<br>IC$_{50}$ (µM)<br>GeoMean |
|---|---|
| 1 | >10 |
| 2 | 2.77 |
| 3 | 4.35 |
| 4 | >10 |
| 5 | 1.6 |
| 6 | 5.31 |
| 7 | 5.8 |
| 8 | >10 |
| 9 | 5.86 |
| 10 | >10 |
| 11 | 0.56 |
| 12 | >10 |
| 13 | 3.6 |
| 14 | 7.75 |
| 15 | 2.16 |
| 16 | 0.82 |
| 17 | 4.07 |

TABLE 2-continued

Electrophysiologic Assessment for Human Cav3.2 Channels

| Example | Human Ca$_v$3.2<br>−77 mV<br>IC$_{50}$ (µM)<br>GeoMean |
|---|---|
| 18 | 9.1 |
| 19 | 1.1 |
| 21 | 1.0 |
| 22 | >10 |

(iii) In Vivo Data—Capsaicin Induced Secondary Mechanical Hyperalgesia Model

Sprague Dawley rats were briefly restrained, and capsaicin was administered at 10 µg in 10 µL of vehicle by intraplantar injection into the center of the right hind paw. Secondary mechanical hyperalgesia (SMH) was measured at the heel away from the site of injection 180 minutes following capsaicin exposure. Compounds and gabapentin (positive control), were administered p.o. 60 minutes before testing (2 hours after capsaicin) or i.p. 30 minutes before testing (2.5 hours after capsaicin). SMH was measured using calibrated von Frey filaments (Stoelting, Woodale, Ill.). Following the 1 hour habituation in the testing room, rats were moved to individual plexiglass chambers that sit on top of a wire mesh to allow for access for stimulation of the plantar surface of the hind paws. Rats were allowed to acclimate to the new chambers for 15 minutes before the onset of testing. The paw withdrawal threshold was determined by increasing and decreasing stimulus intensity (force: g) and calculated using Dixon's up-down method (Chaplan, S R; et al. J. Neuroscience Methods 1994; 53: 55-63). The filaments (maximum force of 15.0 g) were held in place for 8 seconds or until there was a withdrawal response from the mechanical stimulation.

Table 3 lists percent inhibition values relative to vehicle for compounds of the present invention.

TABLE 3

Mechanical Hyperalgesia Model

| Example | % inhibition @<br>30 mg/kg p.o. |
|---|---|
| 3 | 31 |
| 4 | 19 |
| 6 | 74 |
| 7 | 19 |
| 12 | 41 |
| 13 | 60 |
| 14 | 52 |
| 18 | 5 |
| 23 | −2 |
| 24 | 52 | d. Methods of Using the Compounds

One embodiment of the present invention provides a method of treating pain in a subject in need thereof. The method comprises administering to the subject, including a mammal, such as a human, a therapeutically suitable amount of a compound of formula (I), or a pharmaceutically acceptable salt thereof. Conditions related to pain include acute pain, chronic pain, neuropathic pain, inflammatory pain, visceral pain, cancer pain, allodynia, fibromyalgia, sciatica, back pain, and headache pain including migraine, or combinations thereof. Preferably, the method comprises administering to the mammal a therapeutically effective amount of any of the compounds as described herein, or a pharmaceutically acceptable salt thereof. In certain embodiments, the method comprises administering to the mammal a therapeutically effective amount of any of the compounds as described herein, or a pharmaceutically acceptable salt thereof, in combination with one or more of the following: nonsteroidal anti-inflammatory drug (NSAID), opioid analgesic, barbiturate, benzodiazepine, histamine antagonist, sedative, skeletal muscle relaxant, transient receptor potential ion channel antagonist, α-adrenergic, tricyclic antidepressant, anticonvulsant, tachykinin antagonist, muscarinic antagonist, cyclooxygenase-2 selective inhibitor, neuroleptic, vanilloid receptor agonist, vanilloid receptor antagonist, β-adrenergic, local anesthetic, corticosteroid, 5-HT receptor agonist, 5-HT receptor antagonist, 5-HT$_{2A}$ receptor antagonist, cholinergic analgesic, α$_2$δ ligand such as gabapentin or pregabalin, cannabinoid receptor ligand, metabotropic glutamate subtype 1 receptor antagonist, serotonin reuptake inhibitor, norepinephrine reuptake inhibitor, dual serotonin-noradrenaline reuptake inhibitor, Rho kinase inhibitor, inducible nitric oxide synthase inhibitor, acetylcholinesterase inhibitor, prostaglandin E$_2$ subtype 4 antagonist, leukotriene B4 antagonist, 5-lipoxygenase inhibitor, sodium channel blocker, 5-HT3 antagonist, N-methyl-D-aspartic acid receptor antagonist, and phosphodiesterase V inhibitor.

Yet another embodiment of the present invention relates to a method for providing a method for treating disorders of the central nervous system including stroke, epilepsy, manic depression, bipolar disorders, depression, anxiety, schizophrenia, migraine, and psychoses; neural degenerative disorders including Alzheimer's disease, AIDS related dementia, Parkinson's disease, neuropathy caused by head injury, and dementia caused by cerebrovascular disorders; disorders of the lower urinary tract including overactive bladder, prostatis, prostadynia, interstitial cystitis, and benign prostatic hyperplasia; disorders caused by psychogenic stress including bronchial asthma, unstable angina, and hypersensitive colon inflammation; cardiovascular disorders including hypertension, atherosclerosis, heart failure, and cardiac arrhythmias; drug addiction withdrawal symptoms, including ethanol addiction withdrawal symptoms; skin disorders including pruritis and allergic dermatitis, inflammatory bowel disease; cancer; diabetes; and infertility and sexual dysfunction in a mammal in need of such treatment. This method comprises administering to the mammal (including human) a therapeutically effective amount of a compound of the invention or a pharmaceutically acceptable salt thereof.

Calcium channel blockers have been associated with a slightly greater decreased risk of stroke compared to other types of antihypertensive agents (Angeli, F; et al. American Journal of Hypertension 2004; 17: 817-822). The enhanced effect did not correlate with differences in systolic blood pressure and the mechanism of action remains unknown. However, calcium channel blockers have been associated with blockade of central neuronal calcium influx and subsequent ischemic injury in two rodent models (Barone, F C; et al. Stroke 1995; 26: 1683-1690). In another model of global ischemia, a calcium channel blocker offered neuroprotection although not permanently (Colbourne, F; et al. Stroke 1999; 30: 662-668). Additionally, diminished progression of carotid atherosclerosis has been observed with calcium channel blocker use (Zanchetti, A; et al. Circulation 2002; 106: r47-r52).

An increase in intracellular calcium concentration has been correlated with seizure activity (Heinemann, U; et al. Exp. Brain Res. 1977; 27: 237-243). Several studies have indicated that calcium channel blockers produce anticonvulsant activity (Vezzani, A; et al. Neuropharmacology 1988; 27: 451-458. Otoom, S; et al. Fundamental & Clinical Pharmacology 2006; 20: 115-119.).

Calcium channel blockers have been evaluated in the treatment of bipolar disorders and manic depression for decades. There are suggestions that the calcium channel subtype has influence on efficacy of these disorders (Gitlin, M. Molecular Psychiatry 2006; 11: 227-240. Levy, N A; et al. Bipolar Disorders 2000; 2: 108-119.).

Calcium channel blockers have also been associated with the treatment of anxiety and depression (Saade, S; et al. Pharmacology, Biochemistry and Behavior 2003; 74: 269-278).

Antischizophrenic drugs have been found to be calcium channel antagonists (Gould, R J; et al. Proc. Natl. Acad. Sci. USA 1983; 80: 5122-5125). Other calcium channel blockers have been suggested for the treatment of schizophrenia (Tort, A B L; et al. Psychopharmacology 2005; 177: 344-348).

Migraines are treated with calcium channel blockers (Arulmoshi, D K; et al. Vascular Pharmacology 2005; 43: 176-187. Gladstone, J P; et al. Expert Rev. Neurotherapeutics 2003; 3: 845-872.).

Disorders of the lower urinary tract including overactive bladder, prostatis, prostadynia, interstitial cystitis, and benign prostatic hyperplasia can be treated with calcium channel blockers (Fraser, M O; et al. US20050148587, 2005).

Ethanol withdrawal syndrome is decreased with calcium channel blockers (Little, H J; et al. Life Sciences 1986; 39: 2059-2065).

Several cardiac disorders are treated with calcium channel blockers. Atherosclerosis may be reduced by a decrease in free radical-mediated damage as a result of influence on the biophysical properties of membranes (Mason, R P; et al. Biochemical Pharmacology 1998; 55: 1843-1852). Hypertension and angina are both successfully treated with calcium channel blockers (Croom, K F; et al. Drugs 2006; 66: 497-528).

There is data suggesting that calcium channel blockers inhibit the proliferation of cancer cells (Gray, L S; et al. WO200059882, 2000.).

Calcium channels have been suggested as a target for the treatment of diabetes (Bhattacharjee, A; et al. Endocrinology 1997; 138: 3735-3740).

Ion channels including calcium channels play an important role in sperm physiology and fertilization (Darszon, A; et al. Physiological Reviews 1999; 79: 481-510).

Calcium channel blockers modulate inflammation (Bilici, D; et al. Pharmacological Research 2001; 44: 527-531).

Increased calcium levels in neurones has been implicated in Alzheimer's disease. Two suggested mechanisms of increased calcium influx are that β-amyloid may form calcium permeable channels (Bhatia, R; et al. FASEB J. 2000; 14: 1233-1243) or a G-protein-coupled receptor may be activated by β-amyloid (Lorton, D. Mech. Ageing Dev. 1997; 94: 199-211).

Neurodegenerative diseases, including Parkinson's and Alzheimer's diseases can be modulated by calcium channel blockers (Rodnitzky, R L Drugs 1999; 57: 845-849. Vagnucci, A H; et al. The Lancet 2003; 361: 605-608. Veng, L M; et al. Molecular Brain Research 2203; 110: 193-202. Geldenhuys, W J; et al. Bioorganic and Medicinal Chemistry 2007; 15: 1525-1532. Cavalli, A; et al. J. Med. Chem. 2008; 51: 347-372.)

Actual dosage levels of active ingredients in the pharmaceutical compositions of this invention can be varied so as to obtain an amount of the active compound(s) that is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

Compounds of the invention can also be administered as a pharmaceutical composition comprising the compounds of interest in combination with one or more pharmaceutically acceptable carriers. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or other animal range from about 0.01 mg/kg body weight to about 100 mg/kg body weight. More preferable doses can be in the range of from about 0.01 mg/kg body weight to about 30 mg/kg body weight. If desired, the effective daily dose can be divided into multiple doses for purposes of administration. Consequently, single dose compositions may contain such amounts or submultiples thereof to make up the daily dose.

e. Pharmaceutical Compositions

The present invention further provides pharmaceutical compositions that comprise compounds of the present invention or a pharmaceutically acceptable salt or solvate thereof. The pharmaceutical compositions comprise compounds of the present invention that may be formulated together with one or more non-toxic pharmaceutically acceptable carriers.

Another aspect of the present invention is a pharmaceutical composition comprising compounds of the invention, or a pharmaceutically acceptable salt thereof, and one or more pharmaceutically acceptable carriers, alone or in combination with one or more nonsteroidal anti-inflammatory drugs (NSAID), opioid analgesics, barbiturates, benzodiazepines, histamine antagonists, sedatives, skeletal muscle relaxants, transient receptor potential ion channel antagonists, α-adrenergics, tricyclic antidepressants, anticonvulsants, tachykinin antagonists, muscarinic antagonists, cyclooxygenase-2 selective inhibitors, neuroleptics, vanilloid receptor agonists, vanilloid receptor antagonists, β-adrenergics, local anesthetics, corticosteroids, 5-HT receptor agonists, 5-HT receptor antagonists, 5-HT$_{2A}$ receptor antagonists, cholinergic analgesics, α$_2$δ ligands such as gabapentin or pregabalin, cannabinoid receptor ligands, metabotropic glutamate subtype 1 receptor antagonists, serotonin reuptake inhibitors, norepinephrine reuptake inhibitors, dual serotonin-noradrenaline reuptake inhibitors, Rho kinase inhibitors, inducible nitric oxide synthase inhibitors, acetylcholinesterase inhibitors, prostaglandin E$_2$ subtype 4 antagonists, leukotriene B4 antagonists, 5-lipoxygenase inhibitors, sodium channel blockers, 5-HT3 antagonists, N-methyl-D-aspartic acid receptor antagonists, and phosphodiesterase V inhibitors.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally" as used herein, refers to modes of administration which include intravenous, intramuscular, intraperitoneal, intrasternal, subcutaneous and intraarticular injection and infusion.

The term "pharmaceutically acceptable carrier" as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents which delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., Methods in Cell Biology, Volume XIV, Academic Press, New York, N.Y. (1976), p. 33 et seq.

Dosage forms for topical administration of a compound of this invention include powders, sprays, ointments and inhalants. The active compound may be mixed under sterile conditions with a pharmaceutically acceptable carrier and any needed preservatives, buffers or propellants which may be required. Ophthalmic formulations, eye ointments, powders and solutions are also contemplated as being within the scope of this invention.

The compounds of the present invention can be used in the form of pharmaceutically acceptable salts derived from inorganic or organic acids. The phrase "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio.

Pharmaceutically acceptable salts are well known in the art. For example, S. M. Berge et al. describe pharmaceutically acceptable salts in detail in (J. Pharmaceutical Sciences, 1977, 66: 1 et seq). The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, malate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts can be prepared in situ during the final isolation and purification of compounds of this invention by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylammonium, dimethylammonium, trimethylammonium, triethylammonium, diethylammonium, ethylammonium and the like. Other representative organic amines useful for the formation of base addition salts include ethylenediamine, ethanolamine, diethanolamine, piperidine, piperazine and the like.

The term "pharmaceutically acceptable prodrug" or "prodrug" as used herein, represents those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use.

The present invention contemplates compounds of the invention formed by synthetic means or formed by in vivo biotransformation of a prodrug.

The compounds of the invention can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

f. General Synthesis

This invention is intended to encompass compounds of the invention when prepared by synthetic processes or by metabolic processes. Preparation of the compounds by metabolic processes includes those occurring in the human or animal body (in vivo) or processes occurring in vitro.

The compounds of the invention may be prepared by a variety of processes well known for the preparation of compounds of this class. For example, the compounds of the invention wherein the groups $Ar^1$, n, $R^1$, X, and Y, have the meanings as set forth in the summary section unless otherwise noted, can be synthesized as shown in Schemes 1-4.

Abbreviations which have been used in the descriptions of the Schemes and the Examples that follow are: Boc for t-butoxy carbonyl; Bu for butyl; Et for ethyl, EtOH for ethanol; DMF or N,N-dimethylformamide; DMSO for dimethyl sulfoxide; KOtBu for potassium tert-butoxide; MeOH for methanol; $NEt_3$ for triethylamine; Ph for phenyl; psi for pounds per square inch; tBu for tert-butyl; and THF for tetrahydrofuran.

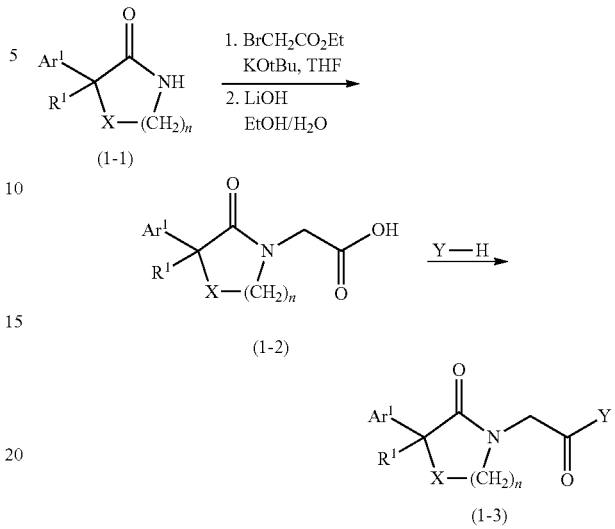

Scheme 1

Compounds of formula (1-3), wherein $Ar^1$, n, $R^1$, X and Y are as defined in formula (I), may be prepared as illustrated in Scheme 1. The treatment of compounds of formula (1-1) with $BrCH_2COEt$ in the presence of a base such as potassium t-butoxide, potassium hydride, or sodium ethoxide in a solvent such as tetrahydrofuran or dioxane at a temperatures of 20-100° C. for 4 to 24 hours supplies the corresponding alkylated lactam. Subsequent treatment with a base such as lithium hydroxide, sodium hydroxide, or potassium hydroxide in a mixture of ethanol and water at 20-100° C. for 1 to 12 hours provides the corresponding carboxylic acid of formula (1-2). Coupling of carboxylic acid (1-2) with H—Y, wherein the H is a hydrogen on a nitrogen atom contained on a primary or secondary amine or as part of a heterocyclic ring, forms an amide bond and yields compounds of formula (1-3) which are representative of compounds of formula (I). Examples of conditions known to generate amides from a mixture of a carboxylic acid and an amine include but are not limited to adding a coupling reagent such as but not limited to $N^1$(ethylimino)methylene)-$N^3$,$N^3$-dimethylpropane-1,3-diamine hydrochloride (EDCI), 1,3-dicyclohexylcarbodiimide (DCC), bis(2-oxo-3-oxazolidinyl)phosphinic chloride (BOPCl), O-(7-azabenzotriazol-1-yl)-N,N,N',N'-tetramethyluronium hexafluorophosphate (HATU), O-benzotriazol-1-yl-N,N,N',N'-tetramethyluronium tetrafluoroborate (TBTU), and 2-(1H-benzo[d][1,2,3]triazol-1-yl)-1,1,3,3-tetramethylisouronium hexafluorophosphate(V) (HBTU). The coupling reagents may be added as a solid, a solution or as the reagent bound to a solid support resin. In addition to the coupling reagents, auxiliary-coupling reagents may facilitate the coupling reaction. Auxiliary coupling reagents that are often used in the coupling reactions include but are not limited to N,N-dimethylpyridin-4-amine (DMAP), 1-hydroxy-7-azabenzotriazole (HOAT) and 1-hydroxybenzotriazole hydrate (HOBT). The reaction may be carried out optionally in the presence of a base such as triethylamine or diisopropylethylamine. The coupling reaction may be carried out in solvents such as but not limited to tetrahydrofuran, N,N-dimethylformamide, dichloromethane, and ethyl acetate. The reaction may be conducted at ambient or elevated temperatures.

Alternatively, compounds of formula (1-3) may be prepared from compounds of formula (1-2) by first forming the corresponding acid chloride. Compounds of formula (1-2), may be treated with oxalyl chloride or thionyl chloride in a solvent such as dichloromethane or toluene at room temperature over 1 to 12 hours to form the intermediate acid chloride. Subsequent treatment with H—Y affords compounds of formula (1-3). Less reactive amines may require elevated temperatures to achieve complete reaction, and this can be realized in a solvent such as dichloroethane or toluene at temperatures of 30-100° C. over 1-12 hours.

Compounds of formula H—Y can be diamines. A protecting group can be present on the amine where the coupling reaction is not desired. Following the amide bond coupling reaction, a deprotection step well known to one skilled in the art can reveal the previously protected amine.

Scheme 2

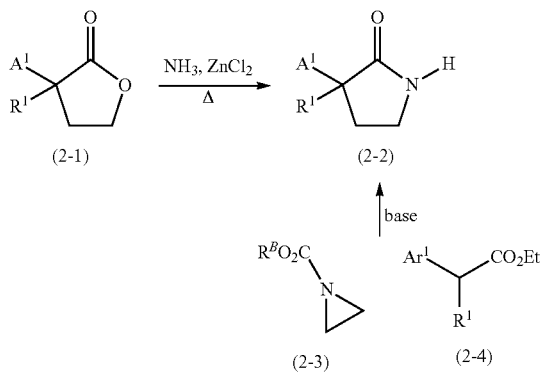

Compounds of formula (2-2) wherein $Ar^1$ and $R^1$ are as described in formula (I) which are representative of compounds of formula (1-1) are prepared with the following procedures. Furanones of formula (2-1) can be treated with ammonia and zinc chloride in an autoclave at temperatures of 150-250° C. for 12 to 36 hours to produce compounds of formula (2-2).

Compounds of formula (2-2) can also be prepared by combining compounds of formula (2-3) and formula (2-4) at or near 0° C., wherein $R^B$ is methyl or ethyl, in the presence of a base such as lithium diisopropylamide or the sodium salt of triphenylmethane in a solvent such as tetrahydrofuran as described in the literature (Stamm, H.; et al. Chem. Ber. 1981, 114, 32-48.) and gradually allowed to warm to room temperature.

Scheme 3

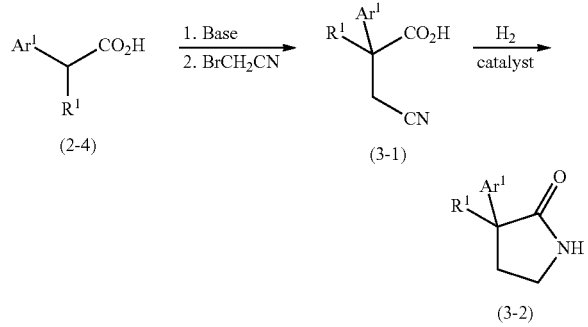

Compounds of formula (3-2) wherein $Ar^1$ and $R^1$ are as described in formula (I) which are representative of compounds of formula (1-1) are prepared by the following sequence. Compounds of formula (2-4), wherein $R^1$ is aryl or heteroaryl, are dissolved in a base such as tetrahydrofuran or dioxane, cooled to a temperature less than −40° C., and treated with a base such as lithium bis(trimethylsilyl)amide or lithium diisopropylamine. After warming to or near 0° C., the reaction mixture is cooled to less than −40° C., and then a solution of bromoacetonitrile is added. After gradually warming to room temperature over 2 or more hours, compounds of formula (3-1) are obtained. Compounds of formula (3-1) are hydrogenated (15-100 pounds per square inch) for 4 to 24 hours in a solvent such as acetic acid or ethanol, in the presence of a catalyst such as platinum oxide to supply compounds of formula (3-2). Alternatively, the reduction and subsequent cyclization from compounds of formula (3-1) to compounds of formula (3-2) can be accomplished with hydrogen and a catalyst such as Raney®-nickel in a solvent mixture of ammonia in methanol.

Scheme 4

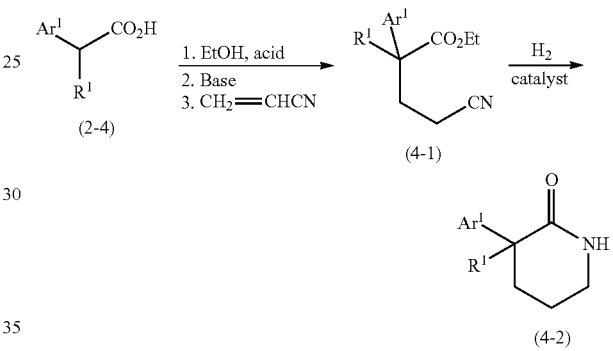

Compounds of formula (4-2) wherein $Ar^1$ and $R^1$ are as described in formula (I) which are representative of compounds of formula (1-1) are prepared by the following sequence. Compounds of formula (2-4), wherein $R^1$ is alkyl, aryl, or heteroaryl, are dissolved in ethanol and treated with sulfuric acid at reflux over 4-16 hours. The intermediate ester can be dissolved in a solvent such as dioxane or tetrahydrofuran and treated with a base such as sodium ethoxide, sodium methoxide, or sodium t-butoxide for 30 minutes to 2 hours at a temperature of 20 to 60° C. Addition of acrylonitrile with continued heating at 40-80° C. for an additional 30 minutes to 2 hours furnishes compounds of formula (4-1). The reduction and subsequent cyclization from compounds of formula (4-1) to compounds of formula (4-2) can be accomplished by hydrogenation (15-50 pounds per square inch) in the presence of a catalyst such as Raney®-nickel in a solvent mixture of ammonia in methanol.

It will be appreciated that the synthetic schemes and specific examples as illustrated in the Examples section are illustrative and are not to be read as limiting the scope of the invention as it is defined in the appended claims. All alternatives, modifications, and equivalents of the synthetic methods and specific examples are included within the scope of the claims.

Optimum reaction conditions and reaction times for each individual step may vary depending on the particular reactants employed and substituents present in the reactants used. Unless otherwise specified, solvents, temperatures and other reaction conditions may be readily selected by one of ordinary skill in the art. Specific procedures are provided in the Examples section. Reactions may be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or may be prepared by one skilled in the art from commercially available materials using methods described in the chemical literature.

Routine experimentations, including appropriate manipulation of the reaction conditions, reagents and sequence of the synthetic route, protection of any chemical functionality that may not be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which may be found in T. Greene and P. Wuts, Protecting Groups in Chemical Synthesis ($3^{rd}$ ed.), John Wiley & Sons, NY (1999), which is incorporated herein by reference in its entirety. Synthesis of the compounds of the invention may be accomplished by methods analogous to those described in the synthetic schemes described hereinabove and in specific examples.

Starting materials, if not commercially available, may be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound of the invention is required, it may be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound of the invention is required, it may be obtained by carrying out one of the above procedures using a pure geometric isomer as a starting material, or by resolution of a mixture of the geometric isomers of the compound or intermediates using a standard procedure such as chromatographic separation.

g. EXAMPLES

The compounds and processes of the present application will be better understood by reference to the following Examples, which are intended as an illustration of and not a limitation upon the scope of the application. Compounds of the application were named by ACD/ChemSketch version 5.01 (developed by Advanced Chemistry Development, Inc., Toronto, ON, Canada) or were given names consistent with ACD nomenclature or were named by Stuct=Name naming algorithm in ChemDraw Ultra 9.0.7 (developed by CambridgeSoft, Cambridge, Mass., USA).

Example 1

2-(2-Oxo-3,3-diphenylpiperidin-1-yl)-N-(piperidin-4-yl)acetamide

Example 1A

Ethyl 2,2-diphenylacetate 2,2-Diphenylacetic acid (50 g) was dissolved in ethanol (350 mL). Concentrated sulfuric acid (3 mL) was added, and the mixture was refluxed overnight. After cooling to room temperature, the reaction mixture was concentrated and diluted with diethyl ether. The organic solvent solution was then extracted with water, saturated aqueous sodium bicarbonate solution, and brine. The organic layer was then dried with magnesium sulfate, filtered, and concentrated to obtain the title compound. MS (DCI+) m/z 241 $(M+H)^+$.

Example 1B

Ethyl 4-cyano-2,2-diphenylbutanoate

The product of Example 1A (5.58 g) was dissolved in anhydrous dioxane (15 mL). Sodium ethoxide (1.58 g) was added, and the mixture was heated to 40-50° C. for 30 minutes. Acrylonitrile (1.44 mL) was added dropwise with stirring. The mixture was heated at 60-70° C. for one hour. The dioxane was removed in vacuo, and the residue was taken up in diethyl ether, washed with water and brine, dried with magnesium sulfate, filtered, and concentrated. The crude material was purified by silica gel chromatography (3-10% ethyl acetate/hexane) to obtain the title compound. MS (DCI+) m/z 311 $(M+NH_4)^+$.

Example 1C 3,3-Diphenylpiperidin-2-one

The product of Example 1B (14.4 g, 49.1 mmol) and 7 M ammonia in methanol (150 mL) were added to solvent-washed Raney®-nickel (72.0 g, 1227 mmol), and the mixture was stirred at room temperature for 24 hours under hydrogen (30 pounds per square inch). The mixture was filtered through a nylon membrane, and the filtrate was concentrated. The residue was dissolved in dichloromethane/methanol (1:1) and filtered through diatomaceous earth to remove a greenish residue. The filtrate was concentrated to obtain a solid which was slurried in methanol, filtered, and dried to obtain the title compound. MS (DCI+) m/z 251 $(M+H)^+$.

Example 1D

Ethyl 2-(2-oxo-3,3-diphenylpiperidin-1-yl)acetate

To a solution of the product of Example 1C (2.51 g, 10.00 mmol) in tetrahydrofuran (100 mL) was added potassium tert-butoxide (1.35 g, 12.00 mmol) under nitrogen followed by ethyl 2-bromoacetate (1.22 mL, 11.00 mmol). The reaction mixture was heated to 80° C. and stirred overnight. The reaction mixture was cooled to room temperature, concentrated and then diluted with ethyl acetate. The organic layer was washed with water and brine, dried over magnesium sulfate, filtered and concentrated. Silica gel chromatography eluting with ethyl acetate/hexane (20:80) gave the title compound. MS (DCI+) m/z 338 $(M+H)^+$.

Example 1E 2-(2-Oxo-3,3-diphenylpiperidin-1-yl)acetic acid

The product from Example 1D (1.70 g, 5.04 mmol) was dissolved in ethanol (40 mL). A solution of lithium hydroxide (1.20 g, 50.10 mmol) in water (10 mL) was added, and the reaction was heated to 80° C. for 2 hours. The reaction mixture was cooled to room temperature, concentrated, neutralized with 2 N HCl, and then diluted with ethyl acetate. The organic layer was washed with water and brine, dried over magnesium sulfate, filtered, and then concentrated to give the title compound. MS (DCI+) m/z 310 (M+H)⁺.

Example 1F 2-(2-Oxo-3,3-diphenylpiperidin-1-yl)-N-(piperidin-4-yl)acetamide

To a solution of 2-(2-oxo-3,3-diphenylpiperidin-1-yl)acetic acid, obtained in Example 1E (0.95 g, 3.08 mmol) and tert-butyl 4-aminopiperidine-1-carboxylate (CAS 87120-72-7) in dichloromethane (10 mL) was added O-(7-azabenzotriazol-1-yl)-N,N,N',N'-tetramethyluronium hexafluorophosphate (1.171 g, 3.08 mmol) and diisopropylethylamine (2.6 mL, 13.86 mmol). The reaction mixture was stirred at ambient temperature overnight, then diluted with dichloromethane and washed with 1 N HCl (10 mL), water, 1 N NaOH (10 mL), water, dried over MgSO$_4$, and evaporated to yield tert-butyl 4-(2-(2-oxo-3,3-diphenylpiperidin-1-yl)acetamido)piperidine-1-carboxylate (0.8 g, 60%). To a solution of this product in methanol (10 mL) was added 4 N HCl/dioxane (2 mL), and the reaction mixture was stirred at room temperature for 3 hours. It was concentrated in vacuo and partitioned between 1 N NaOH and dichloromethane. The organic layer was concentrated and chromatographed on an Analogix 15-24 g silica column, eluting with a 2-5% gradient of methanol/dichloromethane to yield the title compound. $^1$H NMR (300 MHz, CDCl$_3$) δ ppm 7.19-7.35 (m, 10H), 6.99 (d, J=6.4 Hz, 1H), 4.01 (s, 2H), 3.75-3.95 (m, 1H), 3.52 (t, J=6.6 Hz, 2H), 3.04-3.14 (m, 2H), 2.63-2.72 (m, 2H), 2.57-2.64 (m, 2H), 1.77-1.95 (m, 4H), 1.37-1.53 (m, 2H); MS (ESI+) m/z 392 (M+H)⁺.

Example 2

3,3-Dimethyl-4-[(2-oxo-3,3-diphenylpiperidin-1-yl)acetyl]piperazin-2-one

To a solution of 2-(2-oxo-3,3-diphenylpiperidin-1-yl)acetic acid (0.15 g, 0.485 mmol) and 3,3-dimethylpiperazin-2-one (CAS 22476-74-0) (0.062 g, 0.485 mmol) in dichloromethane (3 mL) was added O-(7-azabenzotriazol-1-yl)-N,N,N',N'-tetramethyluronium hexafluorophosphate (0.184, 0.485 mmol) and diisopropylethylamine (0.53 mL, 2.91 mmol). The reaction mixture was stirred at ambient temperature overnight and then concentrated followed by chromatographic purification on an Analogix silica gel column eluting with 5% methanol/dichloromethane to yield the title compound. $^1$H NMR (300 MHz, DMSO-d$_6$) δ ppm 8.05-8.11 (m, 1H), 7.16-7.32 (m, 10H), 4.20 (s, 2H), 3.46-3.52 (m, 2H), 3.33-3.41 (m, 2H), 3.16-3.22 (m, 2H), 2.51-2.57 (m, 2H), 1.63-1.75 (m, 2H), 1.60 (s, 6H); MS (DCI+) m/z 420 (M+H)⁺.

Example 3

1-{2-[(4aS,7aS)-Octahydro-6H-pyrrolo[3,4-b]pyridin-6-yl]-2-oxoethyl}-3,3-diphenylpiperidin-2-one

Example 3A (4aS,7aS)-tert-Butyl 6-benzyloctahydro-1H-pyrrolo[3,4-b]pyridine-1-carboxylate To the solution of (4aS,7aS)-6-benzyloctahydro-1H-pyrrolo[3,4-b]pyridine (CAS 151213-39-7) (0.48 g, 2.2 mmol) in methylene chloride (30 mL) was added di-tert-butyl dicarbonate (0.74 g, 3.4 mmol) and triethylamine (0.6 mL, 4.26 mmol) and the reaction mixture was stirred at ambient temperature overnight. The reaction mixture was diluted with methylene chloride and washed with saturated NaHCO$_3$ solution. The organic layer was separated, dried over MgSO$_4$ and concentrated to yield the title compound. $^1$H NMR (300 MHz, CDCl$_3$) δ ppm 7.34 (m, 4 H), 7.22 (m, 1 H), 4.57 (m, 1 H), 3.88 (m, 1 H), 3.66 (dd, 2H), 2.79 (m, 3 H), 2.63 (m, 1 H), 2.50 (m, 1 H), 2.17 (m, 1 H), 1.72 (m, 1 H), 1.56 (m, 9 H), 1.38 (m, 2 H), 1.23 (m, 1 H).

Example 3B (4aS,7aS)-tert-Butyl octahydro-1H-pyrrolo[3,4-b]pyridine-1-carboxylate The product from the Example 3A (0.15 g, 0.5 mmol) in methanol (80 mL) was hydrogenated (30 psi) in the presence of palladium hydroxide on carbon (0.42 g) for 3 hours at room temperature. The reaction mixture was filtered and concentrated to yield the title compound. MS (DCI+) m/z 227(M+H)⁺.

Example 3C

1-{2-[(4aS,7aS)-Octahydro-6H-pyrrolo[3,4-b]pyridin-6-yl]-2-oxoethyl}-3,3-diphenylpiperidin-2-one The title compound was obtained as described in the procedure for Example 1F, substituting the product from Example 3B for tert-butyl 4-aminopiperidine-1-carboxylate. $^1$H NMR (500 MHz, pyridine-d$_5$, temperature 90° C.) δ ppm 7.56-7.61 (m, 4H), 7.25-7.31 (m, 4H), 7.17-7.22 (m, 2H), 4.20-4.42 (m, 1H), 4.08-4.17 (m, 1H), 3.51-3.65 (m, 3H), 3.32-3.50 (m, 3H), 3.05-3.24 (m, 1H), 2.79-2.86 (m, 1H), 2.58-2.69 (m, 2H), 2.41-2.54 (m, 1H), 1.86-2.09 (m, 1H), 1.71-1.79 (m, 2H), 1.39-1.60 (m, 3H), 1.18-1.33 (m, 1H); MS (ESI+) m/z 418 (M+H)⁺.

Example 4

1-{2-[(4aR,7aR)-Octahydro-6H-pyrrolo[3,4-b]pyridin-6-yl]-2-oxoethyl}-3,3-diphenylpiperidin-2-one

Example 4A (4aR,7aR)-tert-Butyl 6-benzyloctahydro-1H-pyrrolo[3,4-b]pyridine-1-carboxylate The title compound was prepared as described for Example 3A replacing (4aS,7aS)-6-benzyloctahydro-1H-pyrrolo[3,4-b]pyridine with (4aR,7aR)-6-benzyloctahydro-1H-pyrrolo[3,4-b]pyridine. $^1$H NMR (300 MHz, CDCl$_3$) δ ppm 7.34(m, 4 H), 7.22(m, 1 H), 4.57(m, 1 H), 3.88(m, 1 H), 3.66 (dd, 2 H), 2.79 (m, 3 H), 2.63 (m, 1 H), 2.50 (m, 1 H), 2.17 (m, 1 H), 1.72 (m, 1 H), 1.56 (m, 9 H), 1.38 (m, 2 H), 1.23 (m, 1 H); MS(DCI) m/z 317(M+H)⁺.

Example 4B (4aR,7aR)-tert-Butyl octahydro-1H-pyrrolo[3,4-b]pyridine-1-carboxylate The title compound was prepared as described for Example 3B replacing (4aS,7aS)-tert-butyl 6-benzyloctahydro-1H-pyrrolo[3,4-b]pyridine-1-carboxylate with (4aR,7aR)-tert-butyl 6-benzyloctahydro-1H-pyrrolo[3,4-b]pyridine-1-carboxylate from Example 4A. $^1$H NMR (500 MHz, pyridine-d$_5$) δ ppm 3.51 (m, 1 H), 3.39 (m, 1 H), 3.24 (m, 1 H), 3.11 (m, 1H), 2.95 (m, 2 H), 2.78 (m, 2 H), 1.97 (m, 2 H), 1.57 (m, 9 H), 1.26 (m, 2 H); MS (DCI) m/z 227(M+H)$^+$.

Example 4C

1-{2-[(4aR,7aR)-Octahydro-6H-pyrrolo[3,4-b]pyridin-6-yl]-2-oxoethyl}-3,3-diphenylpiperidin-2-one The title compound was obtained as described in the procedure for Example 1F, substituting tert-butyl 4-aminopiperidine-1-carboxylate with (4aR,7aR)-tert-butyl octahydro-1H-pyrrolo[3,4-b]pyridine-1-carboxylate from Example 4B. $^1$H NMR (300 MHz, CDCl$_3$) δ ppm 7.17-7.40 (m, 10H), 4.29-4.57 (m, 1H), 3.70-3.90 (m, 1H), 3.37-3.69 (m, 6H), 3.26-3.34 (m, 1H), 2.95-3.04 (m, 1H), 2.54-2.72 (m, 3H), 2.14-2.38 (m, 1H), 1.62-1.90 (m, 4H), 1.46-1.59 (m, 2H); MS (ESI+) m/z 418 (M+H)$^+$.

Example 5

1-{2-[(4aS,7aS)-Octahydro-1H-pyrrolo[3,4-b]pyridin-1-yl]-2-oxoethyl}-3,3-diphenylpiperidin-2-one

Example 5A 1-(2-((4aS,7aS)-6-Benzyloctahydro-1H-pyrrolo[3,4-b]pyridin-1-yl)-2-oxoethyl)-3,3-diphenylpiperidin-2-one The title compound was obtained as described in the procedure for Example 2, substituting 3,3-dimethylpiperazin-2-one with (4aS,7aS)-6-benzyloctahydro-1H-pyrrolo[3,4-b]pyridine (CAS 151213-39-7). MS (ESI+) m/z 508 (M+H)$^+$.

Example 5B

1-{2-[(4aS,7aS)-Octahydro-1H-pyrrolo[3,4-b]pyridin-1-yl]-2-oxoethyl}-3,3-diphenylpiperidin-2-one The product from Example 5A (415.8 mg, 0.819 mmol) in trifluoroethanol (4 mL) was added to 20% palladium hydroxide on carbon, wet (83 mg, 0.592 mmol) in an 8 mL pressure bottle and stirred under hydrogen (60 psi) at 50° C. for 2 hours. The reaction mixture was concentrated and chromatographed on an Analogix silica column eluting with 5% methanol/dichloromethane. $^1$H NMR (500 MHz, pyridine-d$_5$) δ ppm 7.58-7.68 (m, 4H), 7.32-7.38 (m, 4H), 7.24-7.30 (m, 2H), 5.01-5.58 (m, 1H), 4.48-4.81 (m, 1H), 3.85-4.15 (m, 1H), 3.45-3.84 (m, 6H), 3.08-3.22 (m, 1H), 2.57-2.70 (m, 3H), 2.22-2.53 (m, 1H), 1.66-1.86 (m, 3H), 1.54-1.65 (m, 1H), 1.42-1.54 (m, 1H), 1.28-1.43 (m, 1H); MS (ESI+) m/z 418 (M+H)$^+$.

Example 6

1-(2-Hexahydropyrrolo[3,4-c]pyrrol-2(1H)-yl-2-oxoethyl)-3,3-diphenylpiperidin-2-one

Example 6A 1-(2-(5-Benzylhexahydropyrrolo[3,4-c]pyrrol-2(1H)-yl)-2-oxoethyl)-3,3-diphenylpiperidin-2-one The title compound was obtained as described in the procedure for Example 2, substituting 3,3-dimethylpiperazin-2-one with 2-benzyloctahydropyrrolo[3,4-c]pyrrole (Ohnmacht, C J, et al. Journal of Het. Chem. 1983, 20, 321-329). MS (ESI+) m/z 494 (M+H)$^+$.

Example 6B 1-(2-Hexahydropyrrolo[3,4-c]pyrrol-2(1H)-yl-2-oxoethyl)-3,3-diphenylpiperidin-2-one The product from Example 6A was treated with the procedure described in Example 5B to yield the title compound. $^1$H NMR (300 MHz, CDCl$_3$) δ ppm 7.18-7.36 (m, 10H), 4.19 (d, J=15.9 Hz, 1H), 4.02 (d, J=15.9 Hz, 1H), 3.77 (dd, J=12.3, 8.1 Hz, 1H), 3.72 (dd, J=10.6, 8.1 Hz, 1H), 3.47-3.63 (m, 2H), 3.43 (dd, J=12.6, 3.9 Hz, 1H), 3.31 (dd, J=10.8, 4.3 Hz, 1H), 3.06-3.15 (m, 2H), 2.84-2.95 (m, 1H), 2.72-2.80 (m, 3H), 2.59-2.68 (m, 2H), 1.80-1.88 (m, 2H); MS (ESI+) m/z 404 (M+H)$^+$.

Example 7

1-[2-(2,7-Diazaspiro[3.5]non-2-yl)-2-oxoethyl]-3,3-diphenylpiperidin-2-one

Example 7A

Formaldehyde O-benzyl-oxime

O-Benzyl-hydroxylamine hydrochloride (125.0 g, 0.78 mol) was combined with toluene (400 mL) under nitrogen. The resulting slurry was cooled in an ice bath and formalin (37%, 75 mL) was added. A 50% solution of NaOH (70 mL) was added portionwise maintaining an internal temperature of not more than 35° C. After the addition of NaOH was complete, water (100 mL) was added and the reaction mixture was stirred at ambient temperature for 2.5 hours. The layers were then separated and the aqueous layer was extracted with toluene. The combined organic layers were dried over Na$_2$SO$_4$, filtered and concentrated in vacuo. The resulting oil was distilled (65-70° C., 10 torr) to obtain formaldehyde O-benzyl-oxime. $^1$H NMR (400 MHz, CDCl$_3$) δ ppm 5.12-5.13 (s, 2 H) 6.46 (d, J=8.23 Hz, 1 H) 7.08 (d, J=8.23 Hz, 1 H) 7.28-7.35 (m, 1 H) 7.36 (dd, J=4.19, 0.62 Hz, 4 H).

Example 7B

1-Benzyl-piperidine-4-carboxylic acid ethyl ester

Ethyl isonipecotate (40.0 mL, 0.26 mol), K$_2$CO$_3$, (55 g, 0.4 mol) and N,N-dimethylformamide (200 mL) were combined under nitrogen. The resulting mixture was cooled in an ice bath and benzyl bromide (31.0 mL, 0.26 mol) was added. The reaction mixture was allowed to stir overnight with warming to ambient temperature. A saturated aqueous solution of NH$_4$Cl (500 mL) was added, and the product was extracted twice with ethyl acetate (1 L and 0.5 L). The combined organic layers were washed with saturated aqueous NH$_4$Cl (500 mL) and brine (500 mL), dried over Na$_2$SO$_4$, filtered, and concentrated in vacuo. The resulting crude product was purified by flash chromatography on silica gel (400 g) eluting with hexane/ethyl acetate (1:0 to 4:1) to obtain 1-benzyl-piperidine-4-carboxylic acid ethyl ester. $^1$H NMR (400 MHz, CDCl$_3$) δ ppm 1.24 (t, J=7.07 Hz, 3 H) 1.69-1.82 (m, 2 H) 1.82-1.92 (m, 2 H) 1.96-2.10 (m, 2 H) 2.20-2.34 (m, 1 H) 2.79-2.91 (m, 2 H) 3.48 (s, 2 H) 4.12 (q, J=7.14 Hz, 2 H) 7.20-7.32 (m, 5 H).

Example 7C

7-Benzyl-2-benzyloxy-2,7-diaza-spiro[3.5]nonan-1-one

Lithium hexamethyldisilazane (180 mL, 0.18 mol, 1 M in tetrahydrofuran) under nitrogen was cooled to not more than 5° C. with a ice bath. A solution of 1-benzyl-piperidine-4-carboxylic acid ethyl ester from Example 7B (40.0 g, 0.16 mol) in tetrahydrofuran (450 mL) was added at such a rate as to keep the internal temperature at not more than 5° C., and the mixture was stirred at not more than 5° C. for 1 hour. A solution of formaldehyde O-benzyl-oxime from Example 7A (20.0 g, 0.15 mol) in tetrahydrofuran (200 mL) was added, and the reaction mixture stirred at not more than 5° C. for 1 hour. A saturated aqueous solution of $NH_4Cl$ (300 mL) was added, and the layers were separated. The aqueous layer was extracted with ethyl acetate (500 mL). The combined organic layers were washed with brine (300 mL), dried over $Na_2SO_4$, filtered and concentrated in vacuo. The resulting residue was purified by flash chromatography on silica gel (300 g) eluting with hexane/ethyl acetate (4:1 to 1:1) to afford the titled compound. $^1$H NMR (400 MHz, $CDCl_3$) δ ppm 1.54-1.63 (m, 2 H) 1.91 (ddd, J=13.17, 9.47, 3.70 Hz, 2 H) 2.03-2.17 (m, 2 H) 2.68-2.77 (m, 2 H) 3.03 (s, 2 H) 3.45 (s, 2 H) 4.93 (s, 2 H) 7.19-7.42 (m, 10 H).

Example 7D

7-Benzyl-2,7-diaza-spiro[3.5]nonan-1-one

A 2-L pressure bottle, equipped with a thermocouple and $H_2$ inlet/outlet, was charged with Raney®-nickel (7.0 g). The Raney®-nickel was washed with methanol (3×, slurry and decant supernatant) and a solution of 7-benzyl-2-benzyloxy-2,7-diaza-spiro[3.5]nonan-1-one from Example 7C (28.3 g, 0.084 mol) in methanol (280 mL) was added. The reaction was placed on a Parr shaker and agitated overnight at 50° C. under an atmosphere of $H_2$ (40 psi). The catalyst was removed by filtration and rinsed with methanol. The solution of product with benzyl alcohol was concentrated in vacuo. The benzyl alcohol was removed by azeotropic distillation, twice adding water (250 mL) and concentrating in vacuo. 2-Propanol was used to chase the water, twice adding 2-propanol (250 mL) and concentrating in vacuo to an oil. Heptane (500 mL) was added and the product was allowed to crystallize. After concentrating in vacuo to a final volume of 100 mL, the product was collected by filtration and washed with heptane (25 mL). Drying in a vacuum oven at 40° C. under a flow of $N_2$ afforded the titled compound as a solid. $^1$H NMR (400 MHz, $CDCl_3$) δ ppm 1.75-1.84 (m, 2H) 1.98-2.08 (m, 2 H) 2.19-2.31 (m, 2 H) 2.71-2.83 (m, 2 H) 3.13 (s, 2 H) 3.50 (s, 2 H) 5.69 (s, 1 H) 7.21-7.38 (m, 5 H).

Example 7E tert-Butyl 7-benzyl-2,7-diazaspiro[3.5]nonane-2-carboxylate

7-Benzyl-2,7-diaza-spiro[3.5]nonan-1-one (17.3 g, 0.075 mol) and tetrahydrofuran (200 mL) were combined under nitrogen. A solution of lithium aluminum hydride (90 mL, 0.09 mol, 1 M in tetrahydrofuran) was added and the reaction mixture heated to reflux. After stirring overnight, the mixture was cooled to ambient temperature and carefully quenched by the addition of $Na_2SO_4 \cdot 10 H_2O$ (100 g). After stirring the resulting mixture for 30 minutes, diatomaceous earth (100 g) was added and stirring was continued for 30 minutes. The solid were filtered off rinsing the cake with tetrahydrofuran (2×100 mL), and the solution of product was concentrated in vacuo. The residue was taken up in dichloromethane (200 mL) and di-tert-butyl dicarbonate (22.0 mL, 0.096 mol) was added. After stirring for 60 hours, the solution was concentrated in vacuo. The residue was purified by flash chromatography on silica gel (500 g) eluting with hexane/ethyl acetate (9:1 to 1:1) to afford the titled compound. $^1$H NMR (400 MHz, $CDCl_3$) δ ppm 1.43 (s, 9 H) 1.69-1.78 (m, J=5.49, 5.49 Hz, 4 H) 2.24-2.41 (m, 4 H) 3.44 (s, 2 H) 3.59 (s, 4 H) 7.20-7.32 (m, 5 H); MS ($DCl/NH_3$) m/z 317.2 $(M+H)^+$.

Example 7F

7-Benzyl-2,7-diazaspiro[3.5]nonane dihydrochloride

To a solution of tert-butyl 7-benzyl-2,7-diazaspiro[3.5]nonane-2-carboxylate (CAS 929301-99-5 WO2007030061) in methanol was added 4 N HCl/dioxane. The mixture was stirred at room temperature for 2 hours. The reaction mixture was then concentrated to obtain the title compound. MS (DCI+) m/z 217 $(M+H)^+$.

Example 7G

1-(2-(7-Benzyl-2,7-diazaspiro[3.5]nonan-2-yl)-2-oxoethyl)-3,3-diphenylpiperidin-2-one The title compound was obtained as described in the procedure for Example 2, substituting 3,3-dimethylpiperazin-2-one with 7-benzyl-2,7-diazaspiro[3.5]nonane dihydrochloride. MS (ESI+) m/z 509 $(M+H)^+$.

Example 7H

1-[2-(2,7-Diazaspiro[3.5]non-2-yl)-2-oxoethyl]-3,3-diphenylpiperidin-2-one

The compound from Example 7G was treated as described for Example 5B to yield the title compound. $^1$H NMR (300 MHz, $CDCl_3$) δ ppm 7.16-7.35 (m, 10H), 3.98 (s, 2H), 3.87 (s, 2H), 3.75 (s, 2H), 3.56 (t, J=6.5 Hz, 2H), 2.74-2.93 (m, 4H), 2.58-2.66 (m, 2H), 1.76-1.89 (m, 6H); MS (ESI+) m/z 418 $(M+H)^+$.

Example 8

2-(2-Oxo-3,3-diphenylpiperidin-1-yl)-N-[(2R)-pyrrolidin-2-ylmethyl]acetamide The title compound was obtained as described in Example 1F substituting tert-butyl 4-aminopiperidine-1-carboxylate with (R)-tert-butyl 2-(aminomethyl)pyrrolidine-1-carboxylate (CAS 259537-92-3). $^1$H NMR (300 MHz, $CDCl_3$) δ ppm 7.19-7.36 (m, 10H), 6.68-6.78 (m, 1H), 4.06 (s, 2H), 3.47-3.61 (m, 2H), 3.37 (ddd, J=12.9, 6.1, 4.7 Hz, 1H), 3.16-3.25 (m, 1H), 3.06 (ddd, J=12.9, 7.7, 5.1 Hz, 1H), 2.85 (t, J=6.7 Hz, 2H), 2.59-2.66 (m, 2H), 1.77-1.89 (m, 3H), 1.66-1.80 (m, 2H), 1.23-1.39 (m, 1H); MS (ESI−) m/z 390 $(M-H)^-$.

Example 9

2-(2-Oxo-3,3-diphenylpiperidin-1-yl)-N-[(2S)-pyrrolidin-2-ylmethyl]acetamide The title compound was obtained as described in Example 1F substituting tert-butyl 4-aminopiperidine-1-carboxylate with (S)-tert-butyl 2-(aminomethyl)pyrrolidine-1-carboxylate (CAS 119020-01-8). $^1$H NMR (300 MHz, CDCl$_3$) δ ppm 7.18-7.36 (m, 10H), 6.71-6.77 (bs, 1H), 4.06 (s, 2H), 3.48-3.59 (m, 2H), 3.37 (ddd, J=12.9, 6.2, 4.6 Hz, 1H), 3.15-3.26 (m, 1H), 3.07 (ddd, J=12.9, 7.7, 5.1 Hz, 1H), 2.85 (t, J=6.7 Hz, 2H), 2.60-2.65 (m, 2H), 1.79-1.89 (m, 3H), 1.65-1.79 (m, 2H), 1.22-1.43 (m, 1H); MS (ESI−) m/z 390 (M−H)$^−$.

Example 10

4-[(2-Oxo-3,3-diphenylpiperidin-1-yl)acetyl]piperazin-2-one

The title compound was obtained as described in Example 2 substituting 3,3-dimethylpiperazin-2-one with 2-piperazinone (CAS 5625-67-2). $^1$H NMR (300 MHz, CDCl$_3$) δ ppm 7.19-7.34 (m, 10H), 5.96-6.15 (bs, 1H), 4.21-4.32 (m, 2H), 4.12-4.21 (m, 2H), 3.82-3.90 (m, 1H), 3.67-3.76 (m, 1H), 3.48-3.60 (m, 2H), 3.36-3.46 (m, 2H), 2.60-2.69 (m, 2H), 1.78-1.93 (m, 2H); MS (ESI+) m/z 392 (M+H)$^+$, 409 (M+NH$_4$)$^+$.

Example 11

N-Azetidin-3-yl-2-(2-oxo-3,3-diphenylpiperidin-1-yl)acetamide

The title compound was obtained as described in Example 1F substituting tert-butyl 4-aminopiperidine-1-carboxylate with tert-butyl 3-aminoazetidine-1-carboxylate. $^1$H NMR (500 MHz, pyridine-d$_5$) δ ppm 7.63 (m, 5 H), 7.32 (m, 5 H), 4.78 (m, 1 H), 4.35 (m, 2 H), 4.21 (m, 1 H), 3.64 (m, 1 H), 3.51 (m, 2 H), 3.08 (m, 1 H), 2.91 (m, 1 H), 2.61 (m, 3 H), 1.71 (m, 2 H); MS (ESI+) m/z 364(M+H)$^+$.

Example 12

1-(2-Oxo-2-piperazin-1-ylethyl)-3,3-diphenylpiperidin-2-one

The title compound was obtained as described in Example 1F substituting tert-butyl 4-aminopiperidine-1-carboxylate with tert-butyl piperazine-1-carboxylate. $^1$H NMR (300 MHz, CDCl$_3$) δ ppm 7.16-7.34 (m, 10H), 4.23 (s, 2H), 3.59-3.67 (m, 2H), 3.50 (t, J=6.5 Hz, 2H), 3.41-3.47 (m, 2H), 2.82-2.90 (m, 4H), 2.60-2.68 (m, 2H), 1.80-1.90 (m, 2H); MS (ESI+) m/z 378 (M+H)$^+$.

Example 13

1-{2-[(1S*,5S*)-3,6-Diazabicyclo[3.2.1]oct-3-yl]-2-oxoethyl}-3,3-diphenylpiperidin-2-one

Example 13A 1-(2-((1S*,5S*)-6-Benzyl-3,6-diazabicyclo[3.2.1]oct-3-yl)-2-oxoethyl)-3,3-diphenylpiperidin-2-one The title compound was obtained as described in Example 2 substituting 3,3-dimethylpiperazin-2-one with (1R*,5S*)-6-benzyl-3,6-diazabicyclo[3.2.1]octane (Bunnelle, W H, et al. J. Med. Chem., 2007, 50, 3627-3644). MS (ESI+) m/z 494(M+H)$^+$.

Example 13B

1-{2-[(1S*,5S*)-3,6-Diazabicyclo[3.2.1]oct-3-yl]-2-oxoethyl}-3,3-diphenylpiperidin-2-one The title compound was prepared as described for Example 5B, substituting 1-(2-((4aS,7aS)-6-benzyloctahydro-1H-pyrrolo[3,4-b]pyridin-1-yl)-2-oxoethyl)-3,3-diphenylpiperidin-2-one with 1-(2-((1S*,5S*)-6-benzyl-3,6-diazabicyclo[3.2.1]octan-3-yl)-2-oxoethyl)-3,3-diphenylpiperidin-2-one. $^1$H NMR (400 MHz, pyridine-d$_5$, temperature 90° C.) δ ppm 7.51-7.60 (m, 4H), 7.24-7.31 (m, 4H), 7.15-7.20 (m, 2H), 4.13-4.39 (m, 3H), 3.65 (d, J =10.4 Hz, 2H), 3.30-3.60 (m, 3H), 2.96-3.29 (m, 1H), 2.72-2.83 (m, 2H), 2.51-2.67 (m, 3H), 1.96-2.14 (m, 1H), 1.49-1.79 (m, 4H); MS (ESI+) m/z 404 (M+H)$^+$.

Example 14

3,3-Bis(4-fluorophenyl)-1-(2-oxo-2-piperazin-1-ylethyl)pyrrolidin-2-one

Example 14A

Ethyl 3-cyano-2,2-bis(4-fluorophenyl)propanoate

To a solution of ethyl 2,2-bis(4-fluorophenyl)acetate (0.28 g, 1.00 mmol) in dry tetrahydrofuran at −78° C. was added lithium bis(trimethylsilyl)amide (1.0 M in hexane) (1.00 mL, 1.00 mmol) dropwise via syringe under nitrogen. The reaction was brought to 0° C. and stirred for one hour. The reaction was re-cooled to −78° C. and then bromoacetonitrile (0.69 mL, 1.00 mmol) was added as a solution in tetrahydrofuran (30 mL). The reaction was stirred for 2 hours while the temperature was allowed to reach room temperature. The reaction was quenched with saturated aqueous ammonium chloride solution and extracted with diethyl ether. The combined organic extracts were washed with brine, dried with MgSO$_4$, filtered, and concentrated. The residue was purified by silica gel chromatography (10% ethyl acetate/hexanes) to obtain the title compound. MS (DCI+) m/z 333 (M+NH$_4$)$^+$.

Example 14B 3,3-Bis(4-fluorophenyl)pyrrolidin-2-one

A solution of the product from Example 14A (20 mg, 0.063 mmol) in acetic acid (4 mL) was added to PtO$_2$ (4.00 mg, 0.018 mmol) in a 50 mL pressure bottle and stirred at room temperature for 12 hours under hydrogen (30 pounds per square inch). The mixture was filtered through a nylon membrane and then concentrated to obtain solid. The solid was slurried in 5% ethyl acetate/hexanes, filtered and dried to give the title compound. MS (DCI+) m/z 274 (M+H)$^+$.

Example 14C

Ethyl 2-(3,3-bis(4-fluorophenyl)-2-oxopyrrolidin-1-yl)acetate

To a solution of the product from Example 14B (0.82 g, 3.00 mmol) in tetrahydrofuran (20 mL) was added potassium tert-butoxide (1.0 M in tetrahydrofuran, 4.5 mL, 4.5 mmol) via syringe under nitrogen followed by ethyl 2-bromoacetate (0.33 mL, 3.00 mmol). The reaction mixture was heated to 80° C. and stirred overnight. The reaction mixture was cooled to room temperature, concentrated and then diluted with ethyl acetate. The reaction mixture was washed with water and brine, dried over magnesium sulfate, filtered and concentrated. The residue was purified with silica gel chromatography eluting with ethyl acetate/hexane (20:80) to obtain the title compound. MS (APCI+) m/z 359.9 (M+H)$^+$.

Example 14D 2-(3,3-Bis(4-fluorophenyl)-2-oxopyrrolidin-1-yl)acetic acid

The product from Example 14C (0.90 g, 2.50 mmol) was dissolved in ethanol (20 mL). A solution of lithium hydroxide (0.57 g, 23.97 mmol) in water (5 mL) was added, and the reaction was heated to 80° C. for 2 hours. The reaction mixture was cooled to room temperature, concentrated, neutralized with 2 N HCl, and then extracted with ethyl acetate. The organic layer was washed with water and brine, dried over magnesium sulfate, filtered, and concentrated to supply the title compound. MS (APCI+) m/z 332.2 (M+H)$^+$.

Example 14E 3,3-Bis(4-fluorophenyl)-1-(2-oxo-2-piperazin-1-ylethyl)pyrrolidin-2-one The title compound was obtained using the procedure described in Example 1F substituting the product from Example 1E with the product from Example 14D and substituting tert-butyl 4-aminopiperidine-1-carboxylate with tert-butyl piperazine-1-carboxylate. $^1$H NMR (300 MHz, CDCl$_3$) δ ppm 7.27-7.36 (m, 4H), 6.94-7.04 (m, 4H), 4.18 (s, 2H), 3.54-3.60 (m, 2H), 3.51 (t, J=6.5 Hz, 2H), 3.37-3.43 (m, 2H), 2.78-2.88 (m, 4H), 2.77 (t, J=6.5 Hz, 2H); MS (ESI+) m/z 400 (M+H)$^+$.

Example 15

3,3-Bis(4-fluorophenyl)-1-{2-[(8aR)-hexahydropyrrolo[1,2-a]pyrazin-2(1H)-yl]-2-oxoethyl}pyrrolidin-2-one The title compound was obtained using the procedure described in Example 2 substituting the product from Example 14D for 2-(2-oxo-3,3-diphenylpiperidin-1-yl)acetic acid and substituting (R)-octahydropyrrolo[1,2-a]pyrazine (CAS 96193-27-0) for 3,3-dimethylpiperazin-2-one. $^1$H NMR (300 MHz, CDCl$_3$) δ ppm 7.27-7.35 (m, 4H), 6.94-7.06 (m, 4H), 4.47-4.70 (m, 1H), 4.27-4.39 (m, 1H), 3.98-4.13 (m, 1H), 3.67-3.90 (m, 1H), 3.42-3.61 (m, 1H), 2.94-3.27 (m, 3H), 2.70-2.86 (m, 3H), 2.35-2.47 (m, 1H), 1.97-2.19 (m, 2H), 1.68-1.93 (m, 4H), 1.28-1.47 (m, 1H); MS (ESI+) m/z 440 (M+H)$^+$.

Example 16

N-Azetidin-3-yl-2-[3,3-bis(4-fluorophenyl)-2-oxopyrrolidin-1-yl]acetamide

The title compound was obtained using the procedure described in Example 1F substituting the product from Example 14D for the product of Example 1E and substituting tert-butyl 3-aminoazetidine-1-carboxylate (CAS 96193-27-0) for tert-butyl 4-aminopiperidine-1-carboxylate. $^1$H NMR (300 MHz, CDCl$_3$) δ ppm 7.21-7.34 (m, 4H), 6.95-7.06 (m, 4H), 4.95-5.73 (m, 2H), 4.61-4.74 (m, 1H), 3.98 (s, 2H), 3.84 (t, J=8.3 Hz, 2H), 3.49 (t, J=6.5 Hz, 2H), 3.40 (t, J=7.5 Hz, 2H), 2.77 (t, J=6.5 Hz, 2H); MS (ESI+) m/z 386 (M+H)$^+$.

Example 17

2-[3,3-Bis(4-fluorophenyl)-2-oxopyrrolidin-1-yl]-N-cyclopropyl-N-piperidin-4-ylacetamide Example 17A tert-Butyl 4-(cyclopropylamino)piperidine-1-carboxylate To a solution of tert-butyl 4-oxopiperidine-1-carboxylate 90.3 g, 1.5 mmol) in dichloroethane (10 mL) was add cyclopropylamine (0.13 mL, 1.95 mmol), sodium triacetoxyborohydride (0.48 g, 2.26 mmol) and a few drops of acetic acid. The reaction mixture was stirred at ambient temperature overnight. The reaction mixture was then diluted with dichloromethane and washed with NaHCO$_3$ solution. The organic phase was separated and then dried over MgSO$_4$. Following concentration, the residue was chromatographed on silica gel eluting with 5% methanol/dichloromethane to yield the title compound. $^1$H NMR (300 MHz, CDCl$_3$) δ ppm 4.03 (d, J=12.21 Hz, 2 H), 2.79 (m, 3 H), 2.14 (m, 1 H), 1.91 (d, J=12.55 Hz, 2 H), 1.69 (m, 2 H), 1.46 (m, 9 H), 1.27 (m, 2 H), 0.47 (m, 2 H), 0.36 (m, 2 H).

Example 17B

2-[3,3-Bis(4-fluorophenyl)-2-oxopyrrolidin-1-yl]-N-cyclopropyl-N-piperidin-4-ylacetamide The title compound was obtained using the procedure described in Example 1F substituting the product from Example 14D for the product of Example 1E and substituting tert-butyl 4-(cyclopropylamino)piperidine-1-carboxylate from Example 17A for tert-butyl 4-aminopiperidine-1-carboxylate. $^1$H NMR (300 MHz, CDCl$_3$) δ ppm 7.28-7.37 (m, 4H), 6.95-7.05 (m, 4H), 4.35 (s, 2H), 4.09-4.23 (m, 1H), 3.53 (t, J=6.4 Hz, 2H), 3.15-3.24 (m, 2H), 2.78 (t, J=6.4 Hz, 2H), 2.71 (td, J=12.3, 2.4 Hz, 2H), 2.47-2.59 (m, 1H), 1.90-2.05 (m, 2H), 1.73-1.83 (m, 2H), 0.86-1.02 (m, 4H); MS (ESI+) m/z 454 (M+H)$^+$.

Example 18

2-[3,3-Bis(4-fluorophenyl)-2-oxopyrrolidin-1-yl]-N-cyclobutyl-N-piperidin-4-ylacetamide Example 18A tert-Butyl 4-(cyclobutylamino)piperidine-1-carboxylate The title compound was prepared as described for the Example 17A replacing cyclopropylamine with cyclobutylamine. $^1$H NMR (300 MHz, CDCl$_3$) δ ppm 4.03 (d, J=8.33 Hz, 2 H), 3.39 (m, 1 H), 2.69 (m, 3 H), 2.23 (m, 2 H), 1.70 (m, 6 H), 1.41 (m, 9 H), 1.25 (m, 2 H).

Example 18B

2-[3,3-Bis(4-fluorophenyl)-2-oxopyrrolidin-1-yl]-N-cyclobutyl-N-piperidin-4-ylacetamide The title compound was obtained using the procedure described in Example 1F substituting the product from Example 14D for the product of Example 1E and substituting tert-butyl 4-(cyclobutylamino)piperidine-1-carboxylate from Example 18A for tert-butyl 4-aminopiperidine-1-carboxylate. $^1$H NMR (400 MHz, pyridine-$d_5$, temperature 120° C.) δ ppm 7.51-7.58 (m, 4H), 6.96-7.04 (m, 4H), 4.28 (s, 2H), 4.06-4.21 (m, 1H), 3.59-3.71 (m, 1H), 3.53 (t, J=6.6 Hz, 2H), 3.09-3.16 (m, 2H), 2.76 (t, J=6.6 Hz, 2H), 2.53-2.69 (m, 4H), 2.18-2.33 (m, 2H), 2.03-2.13 (m, 2H), 1.65-1.76 (m, 1H), 1.47-1.60 (m, 3H); MS (ESI+) m/z 468(M+H)$^+$.

Example 19

2-[3,3-Bis(4-fluorophenyl)-2-oxopyrrolidin-1-yl]-N-cyclopentyl-N-piperidin-4-ylacetamide

Example 19A tert-Butyl 4-(cyclopentylamino)piperidine-1-carboxylate

The title compound was prepared using the procedure described for Example 17A substituting cyclopropylamine with cyclopentylamine. $^1$H NMR (300 MHz, CDCl$_3$) δ ppm 4.07 (d, J=13.56 Hz, 2 H), 3.24 (m, 1 H), 2.76 (m, 3 H), 1.89 (m, J=7.46 Hz, 5 H), 1.71 (m, 3H), 1.45 (s, 9 H), 1.34 (m, 4 H).

Example 19B

2-[3,3-Bis(4-fluorophenyl)-2-oxopyrrolidin-1-yl]-N-cyclopentyl-N-piperidin-4-ylacetamide The title compound was obtained using the procedure described in Example 1F substituting the product from Example 14D for the product of Example 1E and substituting tert-butyl 4-(cyclopentylamino)piperidine-1-carboxylate from Example 19A for tert-butyl 4-aminopiperidine-1-carboxylate. $^1$H NMR (501 MHz, pyridine-$d_5$, temperature 90° C.) δ ppm 7.55-7.58 (m, 4H), 7.02-7.06 (m, 4H), 4.28-4.39 (m, 2H), 3.75-3.85 (m, 1H), 3.54 (t, J=6.5 Hz, 2H), 3.47-3.57 (m, 1H), 3.10-3.13 (m, 2H), 2.76 (t, J=6.5 Hz, 2H), 2.64 (td, J=12.3, 2.6 Hz, 2H), 1.89-2.35 (m, 4H), 1.74-1.87 (m, 2H), 1.60-1.70 (m, 2H), 1.49-1.55 (m, 2H), 1.42-1.50 (m, 2H); MS (ESI+) m/z 482M+H)$^+$.

Example 20

1-[2-(2,7-Diazaspiro[3.5]non-2-yl)-2-oxoethyl]-3,3-bis(4-fluorophenyl)pyrrolidin-2-one

Example 20A 1-(2-(7-Benzyl-2,7-diazaspiro[3.5]nonan-2-yl)-2-oxoethyl)-3,3-bis(4-fluorophenyl)pyrrolidin-2-one 7-Benzyl-2,7-diazaspiro[3.5]nonane dihydrochloride from Example 7F (0.237 g, 0.749 mmol), the product from Example 14D (0.248 g, 0.749 mmol), N$^1$-((ethylimino)methylene)-N$^3$,N$^3$-dimethylpropane-1,3-diamine (0.199 ml, 1.123 mmol) and N-methylmorpholine (0.247 ml, 2.247 mmol) were stirred together in dichloromethane (2 mL). After stirring overnight, the reaction mixture was diluted with dichloromethane (20 mL) and washed with 1 N HCl (10 mL), brine (10 mL), dried over magnesium sulfate and concentrated. The residue was loaded onto a GraceResolv 40 gm silica gel column and the product was eluted with a gradient of 0.4% methanol/dichloromethane containing 0.2 N NH$_3$ to 6% methanol/dichloromethane containing 0.2 N NH$_3$ to yield the title compound. $^1$H NMR (300 MHz, CDCl3) δ ppm 7.39-7.15 (m, 9H), 6.99 (t, J=8.2, 4H), 3.97 (s, 2H), 3.72 (d, J=20.0, 4H), 3.53 (t, J=6.5, 2H), 3.46 (s, 2H), 2.75 (t, J=6.4, 2H), 2.32 (s, 4H), 1.73 (s, 4H); MS (ESI+) m/z 530.2 (M+H)$^+$.

Example 20B

1-[2-(2,7-Diazaspiro[3.5]non-2-yl)-2-oxoethyl]-3,3-bis(4-fluorophenyl)pyrrolidin-2-one The product from Example 20A was treated as described for Example 5B to yield the title compound. $^1$H NMR (500 MHz, pyridine-$d_5$) δ ppm 6.39 (m, 4 H), 5.88 (m, 4 H), 2.97 (s, 2 H), 2.45 (d, J=18.00 Hz, 1 H), 2.34 (t, J=6.41 Hz, 2 H), 1.51 (t, J=6.41 Hz, 6 H), 0.34 (m, 4 H); MS (ESI+) m/z 440 (M+H)$^+$.

Example 21

1-[2-(4-Cyclohexylpiperazin-1-yl)-2-oxoethyl]-3,3-diphenylpyrrolidin-2-one

Example 21A 3,3-Diphenylpyrrolidin-2-one 3,3-Diphenyldihydrofuran-2(3H)-one (3.98 g, 16.70 mmol) and zinc chloride (0.080 g) were placed in an autoclave. Ammonia (8 mL) was added, and the reactor was sealed and heated at 225° C. for 21 hours under an argon atmosphere at an equilibrium pressure of 800 pounds per square inch. The vessel was cooled, the ammonia was vented, and a mixture of solids was obtained. The solid was treated with ethanol (100 mL), filtered and concentrated. Silica gel chromatography eluting with 5% methanol/dichloromethane gave the title compound. MS (DCI+) m/z 238.1 (M+H)$^+$.

Example 21B

Ethyl 2-(2-oxo-3,3-diphenylpyrrolidin-1-yl)acetate

To a solution of the product from Example 21A (1.0 g, 4.21 mmol) in tetrahydrofuran (20 mL) was added potassium tert-butoxide (1.0 M in tetrahydrofuran, 6.3 mL, 6.3 mmol) via syringe under nitrogen followed by ethyl 2-bromoacetate (0.47 mL, 4.21 mmol). The reaction mixture was heated to 80° C. and stirred overnight. The reaction mixture was cooled to room temperature, concentrated, and then diluted with ethyl acetate. The organic layer was washed with water and brine, dried over magnesium sulfate, filtered, and concentrated. Silica gel chromatography eluting with ethyl acetate/hexane (20:80) gave the title compound. MS (DCI+) m/z 324.2 (M+H)$^+$.

Example 21C 2-(2-Oxo-3,3-diphenylpyrrolidin-1-yl)acetic acid

The product from Example 21B (0.92 g, 2.84 mmol) was dissolved in ethanol (20 mL). A solution of lithium hydroxide (0.57 g, 23.8 mmol) in water (5 mL) was added, and the reaction was heated to 80° C. for 2 hours. The reaction mixture was cooled to room temperature, concentrated, neutralized with 2 N HCl, and then diluted with ethyl acetate. The organic layer was washed with water and brine, dried over magnesium sulfate, filtered and then concentrated to give the title compound. MS (DCI+) m/z 296.1 (M+H)+.

Example 21D

1-[2-(4-Cyclohexylpiperazin-1-yl)-2-oxoethyl]-3,3-diphenylpyrrolidin-2-one

The title compound was obtained by the procedure described in Example 2, replacing 2-(2-oxo-3,3-diphenylpiperidin-1-yl)acetic acid with 2-(2-oxo-3,3-diphenylpyrrolidin-1-yl)acetic acid and 3,3-dimethylpiperazin-2-one with 1-cyclohexylpiperazine. $^1$H NMR (300 MHz, CDCl$_3$) δ ppm 7.32 (m, 8 H), 7.24 (m, 2 H), 4.19 (s, 2 H), 3.58 (m, 2 H), 3.51 (t, J=6.44 Hz, 2 H), 3.41 (m, 2 H), 2.81 (t, J=6.44 Hz, 4 H), 2.51 (m, 2 H), 2.41 (m, 2 H), 2.23 (t, J=9.83 Hz, 1 H), 1.79 (d, J=9.16 Hz, 4 H), 1.17 (m, 5 H); MS (ESI), m/z 446(M+H)+.

Example 22

1-[2-(4-Methylpiperazin-1-yl)-2-oxoethyl]-3,3-diphenylpiperidin-2-one

The title compound was obtained by the procedure described in Example 2, replacing 3,3-dimethylpiperazin-2-one with 1-methylpiperazine. $^1$H NMR (300 MHz, CDCl$_3$) δ ppm 7.15-7.36 (m, 10H), 4.23 (s, 2H), 3.61-3.70 (m, 2H), 3.45-3.52 (m, 2H), 2.60-2.68 (m, 2H), 2.39-2.45 (m, 4H), 2.30 (s, 3H), 1.78-1.90 (m, 2H), 1.40-1.50 (m, 2H); MS (ESI), m/z 392(M+H)+.

Example 23

3,3-Bis(4-fluorophenyl)-1-(2-oxo-2-piperazin-1-ylethyl)piperidin-2-one

Example 23A

Ethyl 4-cyano-2,2-bis(4-fluorophenyl)butanoate

To a solution of ethyl 2,2-bis(4-fluorophenyl)acetate (1.55 g, 5.64 mmol) in anhydrous dioxane (10 mL) was added sodium ethoxide (0.38 g, 5.61 mmol), and the reaction was stirred at a temperature between 40-50° C. for 30 minutes. Acrylonitrile (0.35 mL, 5.61 mmol) was added dropwise with stirring, and the reaction was heated at 60-70° C. for an additional 1 hour. The dioxane was removed in vacuo, and the residue was taken up in ether, washed with water and brine, dried with MgSO$_4$, filtered and concentrated. Silica gel chromatography eluting with a gradient of 3% to 10% ethyl acetate/hexane gave the title compound. MS (DCI) m/z 342 (M+NH$_4$)+.

Example 23B 3,3-Bis(4-fluorophenyl)piperidin-2-one

The product from Example 23A (560 mg, 1.700 mmol) as a solution in 7 M ammonia/methanol (20 mL) was added to solvent-washed Raney®-nickel (2800 mg, 47.7 mmol) in a 250 mL stainless steel pressure bottle and stirred at room temperature for 24 hours under hydrogen (30 pounds per square inch). The mixture was filtered through a nylon membrane and was concentrated. The residue was dissolved in methanol/dichloromethane (1:1), filtered and concentrated to give a solid which was slurried in methanol, filtered and dried to give the title compound. MS (DCI) m/z 288 (M+H)+.

Example 23C

Ethyl 2-(3,3-bis(4-fluorophenyl)-2-oxopiperidin-1-yl)acetate

To the product from Example 23B (0.43 g, 1.50 mmol) as a solution in tetrahydrofuran (20 mL) was added potassium tert-butoxide (1.0 M in tetrahydrofuran) (1.80 mL, 1.80 mmol) via syringe under nitrogen followed by the addition of ethyl 2-bromoacetate (0.18 mL, 1.65 mmol). The reaction mixture heated at 80° C. and stirred overnight. The reaction mixture was cooled to room temperature, concentrated, diluted with ethyl acetate, washed with water and brine, dried with MgSO4, filtered and concentrated. Silica gel chromatography eluting with ethyl acetate/hexane (1:4) gave the title compound. MS (DCI) m/z 374 (M+H)+.

Example 23D 2-(3,3-Bis(4-fluorophenyl)-2-oxopiperidin-1-yl)acetic acid

The product from Example 23C (0.40 g, 1.07 mmol) was dissolved in ethanol (20 mL). A solution of lithium hydroxide (0.21 g, 8.57 mmol) in water (5 mL) was added and the reaction was heated to 80° C. for 2 hours. The reaction mixture was cooled to room temperature, concentrated, neutralized with 2 N HCl, and then diluted with ethyl acetate. The organic layer was washed with water and brine, dried over magnesium sulfate, filtered, and then concentrated to give the title compound. MS (DCI) m/z 346 (M+H)+.

Example 23E

Benzyl 4-(2-(3,3-bis(4-fluorophenyl)-2-oxopiperidin-1-yl)acetyl)piperazine-1-carboxylate To a solution of 2-(3,3-bis(4-fluorophenyl)-2-oxopiperidin-1-yl)acetic acid (0.34 g, 1.0 mmol, Example 23D) in CH$_2$Cl$_2$ (15 mL) was added benzyl piperazine-1-carboxylate (0.22 g, 1.0 mmol) under nitrogen. 1-(3-Dimethylaminopropyl)-3-ethylcarbodiimide hydrochloride (0.38 g, 2.0 mmol) and 4-(dimethylamino)pyridine (0.012 g, 0.1 mmol) were added to the reaction, and the mixture was stirred overnight at room temperature. The organic layer was washed with water and brine, dried over MgSO$_4$, filtered, and concentrated. The crude product was purified by chromatography on silica gel (Analogix Intelliflash 280; CH$_3$OH/CH$_2$Cl$_2$, 2:98 eluant) to afford the title compound. $^1$H NMR (300 MHz, CDCl$_3$) δ ppm 7.39-7.31 (m, 5H), 7.30-7.21 (m, 4H), 6.97 (dd, J=9.7, 7.7, 4H), 5.15 (s, 2H), 4.19 (s, 2H), 3.70-3.59 (m, 2H), 3.58-3.37 (m, 8H), 2.64-2.52 (m, 2H), 1.90-1.76 (m, 2H); MS (DCI+) m/z 565 (M+MH$_4$)+.

Example 23F 3,3-Bis(4-fluorophenyl)-1-(2-oxo-2-piperazin-1-ylethyl)piperidin-2-one A 50 mL pressure bottle was charged with tetrahydrofuran (10 mL), the product of Example 23E (0.500 g, 0.913 mmol) and 20% Pd(OH)$_2$—C, wet (0.100 g, 0.712 mmol). The reaction mixture was stirred at 50° C. under an atmosphere of 30 psi H$_2$ for 15 minutes. The mixture was filtered through a nylon membrane and concentrated in vacuo. The crude product was purified by chromatography on silica gel (Analogix Intelliflash 280; 2N NH₄OH in CH₃OH/CH₂Cl₂, 2:98, eluant) to afford the title compound. $^1$H NMR (300 MHz, DMSO-d₆) δ ppm 7.30-7.21 (m, 4H), 7.15-7.05 (m, 4H), 4.17 (s, 2H), 3.45-3.24 (m, 7H), 2.66 (d, J=3.6, 4H), 2.55-2.46 (m, 2H), 1.74-1.60 (m, 2H); MS (DCI⁺) m/z 414 (M+H)⁺.

Example 24

1-(2-Oxo-2-piperazin-1-ylethyl)-3,3-diphenylpyrrolidin-2-one

Example 24A

Benzyl 4-(2-(2-oxo-3,3-diphenylpyrrolidin-1-yl)acetyl)piperazine-1-carboxylate

To a solution of 2-(2-oxo-3,3-diphenylpyrrolidin-1-yl)acetic acid (0.29 g, 1.0 mmol, Example 21C) in CH₂Cl₂ (15 mL) was added benzyl piperazine-1-carboxylate (0.22 g, 1.0 mmol) under nitrogen. 1-(3-Dimethylaminopropyl)-3-ethylcarbodiimide hydrochloride (0.38 g, 2.0 mmol) and 4-(dimethylamino)pyridine (0.012 g, 0.1 mmol) were added, and the reaction mixture was stirred overnight at room temperature. The organic layer was washed with water and brine, dried over MgSO₄, filtered, and concentrated. The crude product was purified by chromatography on silica gel (Analogix Intelliflash 280; CH₃OH/CH₂Cl₂, 2:98 eluant) to yield the title compound. $^1$H NMR (300 MHz, CDCl₃) δ ppm 7.43-7.16 (m, 15H), 5.14 (s, 2H), 4.19 (s, 2H), 3.64-3.23 (m, 10H), 2.81 (t, J=6.5, 2H); MS (DCI⁺) m/z 414 (M+H)⁺.

Example 24B 1-(2-Oxo-2-piperazin-1-ylethyl)-3,3-diphenylpyrrolidin-2-one

A 50 mL pressure bottle was charged with tetrahydrofuran (10 mL), the product from Example 24A (0.450 g, 0.904 mmol) and 20% Pd(OH)₂—C, wet (0.090 g, 0.641 mmol). The reaction mixture was stirred at 50° C. under an atmosphere of 30 psi H₂ for 15 minutes. The mixture was filtered through a nylon membrane and concentrated in vacuo. The crude product was purified by chromatography on silica gel (Analogix Intelliflash 280; 2N NH₄OH in CH₃OH/CH₂Cl₂, 2:98, eluant) to afford the title compound. $^1$H NMR (300 MHz, DMSO-d₆) δ ppm 7.36-7.19 (m, 10H), 4.16 (s, 2H), 3.40-3.25 (m, 7H), 2.73 (t, J=6.5, 2H), 2.68-2.59 (m, 4H); MS (DCI⁺) m/z 364 (M+H)⁺.

Example 25

3,3-Bis(4-chlorophenyl)-1-(2-oxo-2-piperazin-1-ylethyl)pyrrolidin-2-one

Example 25A

Ethyl 2,2-bis(4-chlorophenyl)-3-cyanopropanoate

Ethyl 2,2-bis(4-chlorophenyl)acetate (5.50 g, 17.8 mmol) was dissolved in 100 mL of dry tetrahydrofuran and cooled to −78° C. Lithium bis(trimethylsilyl)amide (1.0 M in hexane, 18.0 mL, 18.0 mmol) was added dropwise via syringe under nitrogen. The reaction was brought to 0° C., stirred for 1 hour, and then cooled to −78° C. A solution of bromoacetonitrile (1.24 mL, 17.8 mmol) dissolved in tetrahydrofuran was added, and the reaction was stirred for 2 hours while warming to room temperature. The reaction was quenched with saturated NH₄Cl solution and extracted with diethyl ether. The organic phase was washed with brine, dried over MgSO4, filtered, and concentrated. Chromatography on silica gel (Analogix Intelliflash 280; 10% ethyl acetate/hexane) yielded the title compound: $^1$H NMR (300 MHz, CDCl₃) δ ppm 7.38-7.32 (m, 4H), 7.22-7.17 (m, 4H), 4.25 (q, J=7.2, 2H), 3.32 (s, 2H), 1.23 (t, J=7.2, 3H); MS (DCI⁺) m/z 365 (M+NH₄)⁺.

Example 25B 3,3-Bis(4-chlorophenyl)pyrrolidin-2-one

A 500 mL stainless steel pressure bottle was charged with a Raney®-nickel 2800/water slurry (23.60 g, 402 mmol), followed by addition of the product from Example 25A (5.90 g, 16.9 mmol) and a solution of 7M NH₃—CH₃OH (30 mL)/CH₃OH (120 mL). The reaction mixture was stirred at ambient temperature under an atmosphere of 30 psi H₂ for 4 hours. The mixture was filtered through a nylon membrane and concentrated in vacuo. The crude product was slurried in 5% ethyl acetate/hexane, and the solid was collected by filtration to yield the title compound. $^1$H NMR (300 MHz, DMSO-d₆) δ ppm 8.13 (s, 1H), 7.41-7.35 (m, 4H), 7.35-7.30 (m, 4H), 3.18 (t, J=6.4, 2H), 2.72 (t, J=6.4, 2H); MS (DCI⁺) m/z 323 (M+NH₄)⁺.

Example 25C

Ethyl 2-(3,3-bis(4-chlorophenyl)-2-oxopyrrolidin-1-yl)acetate

To a suspension of the product from Example 25B (0.76 g, 2.5 mmol) in tetrahydrofuran (40 mL) was added a solution of potassium t-butoxide (1.0 M in tetrahydrofuran, 2.6 mL, 2.6 mmol). After stirring for 30 minutes at room temperature a pale yellow homogeneous solution resulted. To the reaction was added ethyl bromoacetate (0.42 g, 2.5 mmol) and stirring was continued overnight at room temperature. The reaction was concentrated, diluted with ethyl acetate (100 mL), washed with water and brine, dried over MgSO4, filtered and concentrated. The residue was dissolved in minimal amount of dichloromethane and loaded onto a silica gel column. The product was eluted with a gradient of 5% ethyl acetate/hexanes to 50% ethyl acetate/hexanes to afford the title compound.

Example 25D 2-(3,3-Bis(4-chlorophenyl)-2-oxopyrrolidin-1-yl)acetic acid

The product from Example 25C (0.95 g, 2.42 mmol) was dissolved in ethanol/water (4:1, 50 mL) and treated with lithium hydroxide (7.85 g, 328.0 mmol). After stirring for 3 hours at reflux, the reaction was concentrated, diluted with ice/water (50 mL) and neutralized with 1 N HCl. The resulting precipitate was collected by filtration, washed with water (50 mL) and air-dried to afford the title compound.

Example 25E tert-Butyl 4-(2-(3,3-bis(4-chlorophenyl)-2-oxopyrrolidin-1-yl)acetyl)piperazine-1-carboxylate To a solution of the product from Example 25D (0.8 g, 2.2 mmol) in CH₂Cl₂ (30 mL) was added tert-butyl piperazine- 1-carboxylate (0.41 g, 2.2 mmol) under nitrogen. 1-(3-Dimethylaminopropyl)-3-ethylcarbodiimide hydrochloride (0.84 g, 4.4 mmol) and 4-(dimethylamino)pyridine (0.027 g, 0.22 mmol) were added, and the reaction mixture was stirred overnight at room temperature. The reaction mixture was then washed with water and brine, dried over MgSO$_4$, filtered, and concentrated. The crude product was purified by chromatography on silica gel (Analogix Intelliflash 280; (CH$_3$OH/CH$_2$Cl$_2$, 2:98 eluant) to afford the title compound.

Example 25F 3,3-Bis(4-chlorophenyl)-1-(2-oxo-2-piperazin-1-ylethyl)pyrrolidin-2-one To a solution of the product from Example 25E (0.920 g, 1.73 mmol) in CH$_2$Cl$_2$ (20 mL) was added trifluoroacetic acid (2.66 mL, 34.6 mmol) under nitrogen. The reaction mixture was stirred overnight at room temperature. The reaction mixture was concentrated to remove excess trifluoroacetic acid and then diluted with CH$_2$Cl$_2$ (150 ml). The organic layer was washed with saturated aqueous NaHCO$_3$ solution, water, and brine, dried with MgSO$_4$, filtered, and concentrated. Purification by chromatography on silica gel, eluting with 7N NH$_3$ in CH$_3$OH/CH$_2$Cl$_2$, 3:97) yielded the title compound: $^1$H NMR (300 MHz, DMSO-d$_6$) δ ppm 7.42-7.30 (m, 8H), 4.16 (s, 2H), 3.40-3.29 (m, 7H), 2.75-2.59 (m, 6H).

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

We claim:
1. A compound of formula (I):

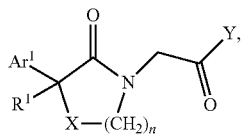

or a pharmaceutically acceptable salt thereof, wherein
n is 2;
X is CH$_2$;
R$^1$ is hydrogen, alkyl, or G$^1$;
Ar$^1$ is aryl or heteroaryl; wherein Ar$^1$ is unsubstituted or further substituted with 1, 2, 3, 4, or 5 substituents independently selected from the group consisting of alkyl, alkenyl, alkynyl, halogen, —CN, —NO$_2$, —OR$^a$, —S(R$^c$), —S(O)(R$^c$), —S(O)$_2$R$^c$, —S(O)$_2$N(R$^b$)$_2$, —C(O)R$^b$, —C(O)O(R$^b$), —C(O)N(R$^b$)$_2$, —N(R$^b$)$_2$, —N(R$^b$)C(O)R$^b$, —N(R$^b$)C(O)O(R$^b$), —N(R$^b$)S(O)$_2$R$^c$, haloalkyl, —(CR$^d$R$^e$)$_m$—OR$^a$, —(CR$^d$R$^e$)$_m$—S(R$^c$), —(CR$^d$R$^e$)$_m$—S(O)(R$^c$), —(CR$^d$R$^e$)$_m$—S(O)$_2$R$^c$, —(CR$^d$R$^e$)$_m$—S(O)$_2$N(R$^b$)$_2$, —(CR$^d$R$^e$)$_m$—C(O)R$^b$, —(CR$^d$R$^e$)$_m$—C(O)O(R$^b$), —(CR$^d$R$^e$)$_m$—C(O)N(R$^b$)$_2$, —(CR$^d$R$^e$)$_m$—N(R$^b$)$_2$, —(CR$^d$R$^e$)$_m$—N(R$^b$)C(O)R$^b$, —(CR$^d$R$^e$)$_m$—N(R$^b$)C(O)O(R$^b$), and —(CR$^d$R$^e$)$_m$—N(R$^b$)S(O)$_2$R$^c$;

R$^a$, at each occurrence, is independently hydrogen, alkyl, haloalkyl, or —(CR$^d$R$^e$)$_m$—O(alkyl);

R$^b$, at each occurrence, is independently hydrogen, alkyl, haloalkyl, or G$^1$;

R$^c$, at each occurrence, is independently alkyl or haloalkyl;

R$^d$ and R$^e$, at each occurrence, are each independently hydrogen, halogen, alkyl, or haloalkyl;

m, at each occurrence, is independently 1, 2, 3, 4, 5, or 6;

Y is (i-a), (i-b), (i-c), (i-d), (i-e), (ii), (iii), (iv), (v), (vi), (vii), (viii), (ix), (x) or (xi):

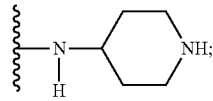

(i-a)

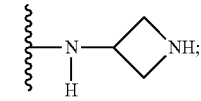

(i-b)

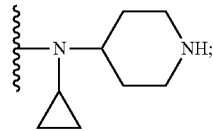

(i-c)

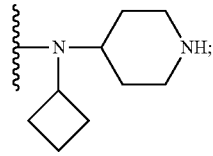

(i-d)

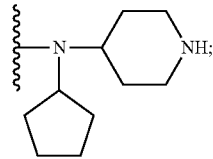

(i-e)

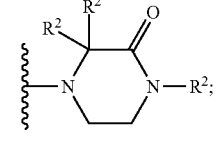

(ii)

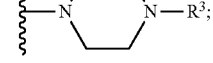

(iii)

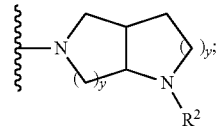

(iv)

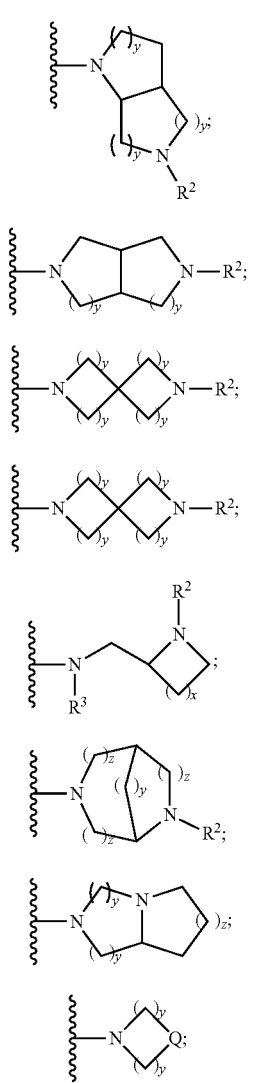

x is 1, 2, or 3;
y at each occurrence, is independently 1 or 2;
z at each occurrence, is independently 0, 1, or 2;
Q is O, S, or $CH_2$;
$R^2$, at each occurrence, is independently hydrogen or alkyl;
$R^3$ is hydrogen, alkyl, or $G^1$; and
$G^1$, at each occurrence, is independently aryl, heteroaryl, heterocycle, cycloalkyl, or cycloalkenyl; wherein each $G^1$ is independently unsubstituted or further substituted with 1, 2, 3, 4, 5, or 6 substituents independently selected from the group consisting of alkyl, alkenyl, alkynyl, halogen, oxo, —CN, —$NO_2$, —$OR^a$, —$S(R^c)$, —$S(O)(R^c)$, —$S(O)_2R^c$, —$S(O)_2N(R^b)_2$, $C(O)R^b$, —$C(O)O(R^b)$, —$C(O)N(R^b)_2$, —$N(R^b)_2$, —$N(R^b)C(O)R^b$, —$N(R^b)C(O)O(R^b)$, —$N(R^b)S(O)_2R^c$, haloalkyl, —$(CR^dR^e)_m$—$OR^a$, —$(CR^dR^e)_m$—$S(R^c)$, —$(CR^dR^e)_m$—$S(O)(R^c)$, —$(CR^dR^e)_m$—$S(O)_2R^c$, —$(CR^dR^e)_m$—$S(O)_2N(R^b)_2$, —$(CR^dR^e)_m$—$C(O)R^b$, —$(CR^dR^e)_m$—$C(O)O(R^b)$, —$(CR^dR^e)_m$—$C(O)N(R^b)_2$, —$(CR^dR^e)_m$—$N(R^b)_2$, —$(CR^dR^e)_m$—$N(R^b)C(O)R^b$, —$(CR^dR^e)_m$—$N(R^b)C(O)O(R^b)$, and —$(CR^dR^e)_m$—$N(R^b)S(O)_2R^c$.

2. The compound or salt according to claim 1, wherein $R^1$ is $G^1$.

3. The compound or salt according to claim 2, wherein $Ar^1$ is aryl, wherein $Ar^1$ is unsubstituted or further substituted with 1, 2, or 3, substituents independently selected from the group consisting of alkyl, alkenyl, alkynyl, halogen, —CN, —$NO_2$, —$OR^a$, —$S(R^c)$, —$S(O)(R^c)$, —$S(O)_2R^c$, —$S(O)_2N(R^b)_2$, —$C(O)R^b$, —$C(O)O(R^b)$, —$C(O)N(R^b)_2$, —$N(R^b)_2$, —$N(R^b)C(O)R^b$, —$N(R^b)C(O)O(R^b)$, —$N(R^b)S(O)_2R^c$, haloalkyl, —$(CR^dR^e)_m$—$OR^a$, —$(CR^dR^e)_m$—$S(R^c)$, —$(CR^dR^e)_m$—$S(O)(R^c)$, —$(CR^dR^e)_m$—$S(O)_2R^c$, —$(CR^dR^e)_m$—$S(O)_2N(R^b)_2$, —$(CR^dR^e)_m$—$C(O)R^b$, —$(CR^dR^e)_m$—$C(O)O(R^b)$, —$(CR^dR^e)_m$—$C(O)N(R^b)_2$, —$(CR^dR^e)_m$—$N(R^b)_2$, —$(CR^dR^e)_m$—$N(R^b)C(O)R^b$, —$(CR^dR^e)_m$—$N(R^b)C(O)O(R^b)$, and —$(CR^dR^e)_m$—$N(R^b)S(O)_2R^c$; and $R^1$ is $G^1$, and $G^1$ is aryl, wherein $G^1$ is unsubstituted or further substituted with 1, 2, or 3 substituents independently selected from the group consisting of alkyl, alkenyl, alkynyl, halogen, oxo, —CN, —$NO_2$, —$OR^a$, —$S(R^c)$, —$S(O)(R^c)$, —$S(O)_2R^c$, —$S(O)_2N(R^b)_2$, $C(O)R^b$, —$C(O)O(R^b)$, —$C(O)N(R^b)_2$, —$N(R^b)_2$, —$N(R^b)C(O)R^b$, —$N(R^b)C(O)O(R^b)$, —$N(R^b)S(O)_2R^c$, haloalkyl, —$(CR^dR^e)_m$—$OR^a$, —$(CR^dR^e)_m$—$S(R^c)$, —$(CR^dR^e)_m$—$S(O)(R^c)$, —$(CR^dR^e)_m$—$S(O)_2R^c$, —$(CR^dR^e)_m$—$S(O)_2N(R^b)_2$, —$(CR^dR^e)_m$—$C(O)R^b$, —$(CR^dR^e)_m$—$C(O)O(R^b)$, —$(CR^dR^e)_m$—$C(O)N(R^b)_2$, —$(CR^dR^e)_m$—$N(R^b)_2$, —$(CR^dR^e)_m$—$N(R^b)C(O)R^b$, —$(CR^dR^e)_m$—$N(R^b)C(O)O(R^b)$, and —$(CR^dR^e)_m$—$N(R^b)S(O)_2R^c$.

4. The compound or salt according to claim 3, wherein $Ar^1$ is aryl, wherein $Ar^1$ is unsubstituted or further substituted with 1, 2, or 3, substituents independently selected from the group consisting of alkyl, alkenyl, alkynyl, halogen, —CN, —$OR^a$, or haloalkyl;

$R^1$ is $G^1$, and $G^1$ is aryl, wherein $G^1$ is unsubstituted or further substituted with 1, 2, or 3 substituents independently selected from the group consisting of alkyl, alkenyl, alkynyl, halogen, —CN, —$OR^a$, or haloalkyl; and Y is (i-a), (i-b), (i-c), (i-d), (i-e), (ii), (iii), (iv), (v), (vi), (vii), (viii), or (ix):

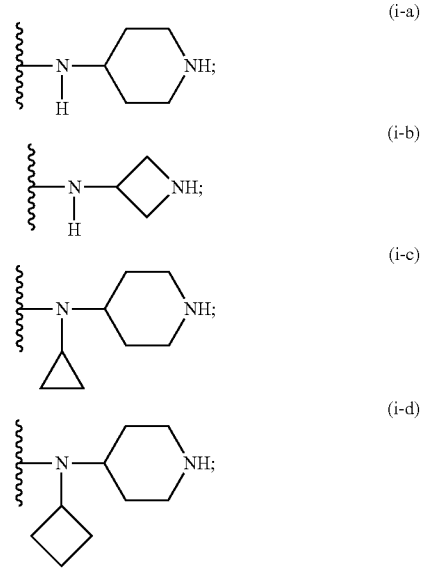

-continued

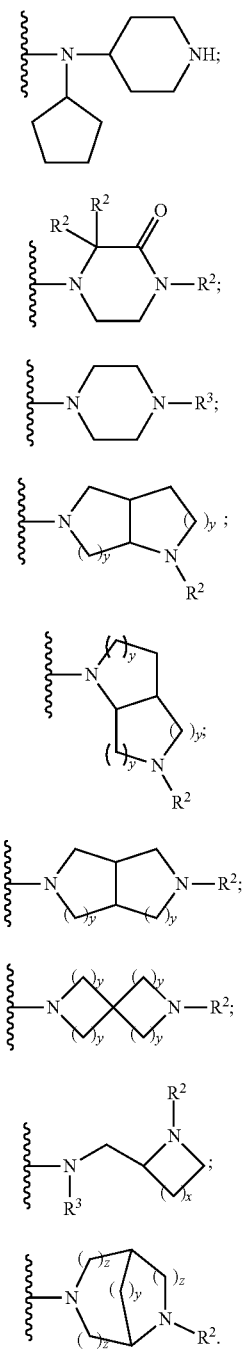

5. The compound or salt according to claim 1, wherein the compound is selected from the group consisting of:

2-(2-oxo-3,3-diphenylpiperidin-1-yl)-N-piperidin-4-ylacetamide;

3,3-dimethyl-4-[(2-oxo-3,3-diphenylpiperidin-1--yl)acetyl]piperazin-2-one;

1-{2-[(4aS,7aS)-octahydro-6H-pyrrolo[3,4-b]pyridin-6-yl]-2-oxoethyl}-3,3-diphenylpiperidin-2-one;

1-{2-[(4aR,7aR)-octahydro-6H-pyrrolo[3,4-b]pyridin-6-yl]-2-oxoethyl}-3,3-diphenylpiperidin-2-one;

1-{2-[(4aS,7aS)-octahydro-1H-pyrrolo[3,4-b]pyridin-1-yl]-2-oxoethyl}-3,3-diphenylpiperidin-2-one;

1-(2-hexahydropyrrolo[3,4-c]pyrrol-2(1H)-yl-2-oxoethyl)-3,3-diphenylpiperidin-2-one;

1-[2-(2,7-diazaspiro[3.5]non-2-yl)-2-oxoethyl]-3,3-diphenylpiperidin-2-one;

2-(2-oxo-3,3-diphenylpiperidin-1-yl)-N-[(2R)-pyrrolidin-2-ylmethyl]acetamide;

2-(2-oxo-3,3-diphenylpiperidin-1-yl)-N-[(2S)-pyrrolidin-2-ylmethyl]acetamide;

4-[(2-oxo-3,3-diphenylpiperidin-1-yl)acetyl]piperazin-2-one;

N-azetidin-3-yl-2-(2-oxo-3,3-diphenylpiperidin-1-yl)acetamide;

1-(2-oxo-2-piperazin-1-ylethyl)-3,3-diphenylpiperidin-2-one;

1-{2-[(1S*,5S*)-3,6-diazabicyclo[3.2.1]oct-3-yl]-2-oxoethyl}-3,3-diphenylpiperidin-2-one;

1-[2-(4-methylpiperazin-1-yl)-2-oxoethyl]-3,3-diphenylpiperidin-2-one; and 3,3-bis(4-fluorophenyl)-1-(2-oxo-2-piperazin-1-ylethyl)piperidin-2-one.

6. A pharmaceutical composition comprising a therapeutically effective amount of a compound of formula (I) according to claim 1, or a pharmaceutically acceptable salt thereof, in combination with a pharmaceutically acceptable carrier.

7. A method of treating pain in a subject in need thereof, comprising: administering to the subject a therapeutically suitable amount of a compound of formula (I) according to claim 1, or a pharmaceutically acceptable salt thereof, wherein the pain is selected from the group consisting of acute pain, chronic pain, neuropathic pain, inflammatory pain, visceral pain, cancer pain, allodynia, fibromyalgia, sciatica, back pain, headache pain including migraine, and combinations thereof.

* * * * *